(12) United States Patent
Fevre et al.

(10) Patent No.: US 10,667,514 B2
(45) Date of Patent: Jun. 2, 2020

(54) ANTIMICROBIAL IONENE COMPOSITIONS WITH A VARIETY OF FUNCTIONAL GROUPS

(71) Applicants: International Business Machines Corporation, Armonk, NY (US); Agency for Science, Technology and Research, Connexis (SG)

(72) Inventors: Mareva B. Fevre, San Jose, CA (US); James L. Hedrick, Pleasanton, CA (US); Nathaniel H. Park, San Jose, CA (US); Victoria A. Piunova, Los Gatos, CA (US); Pang Kern Jeremy Tan, Singapore (SG); Chuan Yang, Hillington Green (SG); Yi Yan Yang, Singapore (SG)

(73) Assignees: INTERNATIONAL BUSINESS MACHINES CORPORATION, Armonk, NY (US); AGENCY FOR SCIENCE, TECHNOLOGY AND RESEARCH, Connexis (SG)

( * ) Notice: Subject to any disclaimer, the term of this patent is extended or adjusted under 35 U.S.C. 154(b) by 55 days.

(21) Appl. No.: 15/839,415

(22) Filed: Dec. 12, 2017

(65) Prior Publication Data
US 2019/0174754 A1 Jun. 13, 2019

(51) Int. Cl.
| | |
|---|---|
| A01N 25/04 | (2006.01) |
| A01N 25/10 | (2006.01) |
| A01N 27/00 | (2006.01) |
| A01N 33/04 | (2006.01) |
| A01N 43/08 | (2006.01) |
| A01N 47/30 | (2006.01) |
| A01N 37/02 | (2006.01) |
| A01N 33/12 | (2006.01) |
| A61Q 17/00 | (2006.01) |

(52) U.S. Cl.
CPC ............ *A01N 33/04* (2013.01); *A01N 25/04* (2013.01); *A01N 25/10* (2013.01); *A01N 27/00* (2013.01); *A01N 33/12* (2013.01); *A01N 37/02* (2013.01); *A01N 43/08* (2013.01); *A01N 47/30* (2013.01); *A01N 2300/00* (2013.01); *A61Q 17/005* (2013.01)

(58) Field of Classification Search
CPC ........ A01N 33/04; A01N 25/10; A01N 25/04; A01N 27/00; A01N 37/02; A01N 33/12; A01N 43/08; A01N 47/30
See application file for complete search history.

(56) References Cited

U.S. PATENT DOCUMENTS

| | | | |
|---|---|---|---|
| 3,632,623 A | 1/1972 | Becke et al. | |
| 4,013,507 A | 3/1977 | Rembaum | |
| 4,032,596 A | 6/1977 | Uffner et al. | |
| 4,094,827 A | * 6/1978 | McEntire | |
| 4,166,894 A | 9/1979 | Schaper | |
| 4,348,536 A | * 7/1982 | Blahak et al. | |
| 4,698,391 A | 10/1987 | Yacobucci et al. | |
| 4,794,031 A | 12/1988 | Leir et al. | |
| 4,883,655 A | 11/1989 | Login et al. | |
| 5,419,897 A | 5/1995 | Drake et al. | |
| 5,681,862 A | 10/1997 | Hollis et al. | |
| 6,767,549 B2 | 7/2004 | Mandeville, III et al. | |
| 6,955,806 B2 | 10/2005 | Fitzpatrick et al. | |
| 8,541,477 B2 | 9/2013 | Alabdulrahman et al. | |
| 2006/0002889 A1 | 1/2006 | Fitzpatrick | |
| 2007/0025954 A1 | 2/2007 | Fitzpatrick et al. | |
| 2007/0106061 A1 | 5/2007 | Zollinger et al. | |
| 2012/0202979 A1 | 8/2012 | Wu | |
| 2013/0281515 A1 | 10/2013 | Coady et al. | |
| 2014/0275469 A1 | 9/2014 | Dhal et al. | |
| 2015/0038392 A1 | 2/2015 | Scheuing et al. | |
| 2016/0374335 A1 | 12/2016 | Chan et al. | |
| 2016/0375150 A1 | 12/2016 | Wu | |

FOREIGN PATENT DOCUMENTS

| | | |
|---|---|---|
| CN | 1192649 A | 9/1998 |
| CN | 1254334 A | 5/2000 |
| CN | 1518621 A | 8/2004 |
| CN | 101426507 A | 5/2009 |
| CN | 101646728 A | 2/2010 |
| CN | 105482105 A | 4/2016 |
| GB | 2 000 164 A | 1/1979 |

(Continued)

OTHER PUBLICATIONS

International Search Report and Written Opinion received for PCT Application Serial No. PCT/IB2018/059622, dated Mar. 28, 2019, 9 pages.
International Search Report and Written Opinion received for PCT Application Serial No. PCT/IB2018/059626, dated Apr. 15, 2019, 8 pages.
International Search Report and Written Opinion received for PCT Application Serial No. PCT/IB2018/059620, dated Mar. 27, 2019, 11 pages.
Liu, et al., Highly potent antimicrobial polyionenes with rapid killing kinetics, skin biocompatibility and in vivo bactericidal activity, Biomaterials, 2017, pp. 36-48, vol. 127.
Williams, et al., Recent advances in the synthesis and structure—property relationships of ammonium ionenes, Progress in Polymer Science, 2009, pp. 762-782, vol. 34.

(Continued)

*Primary Examiner* — Alma Pipic
(74) *Attorney, Agent, or Firm* — Amin, Turocy & Watson, LLP

(57) ABSTRACT

Techniques regarding amine monomers that can form ionene compositions with antimicrobial functionality are provided. For example, one or more embodiments described herein can comprise a monomer, which can comprise a molecular backbone. The molecular backbone can comprise a norspermidine structure. The norspermidine structure can comprise a tertiary amino group. Also, the tertiary amino group can comprise a functional group, and an amino group of the norspermidine structure can be capable of being ionized.

3 Claims, 17 Drawing Sheets
(1 of 17 Drawing Sheet(s) Filed in Color)

(56) References Cited

FOREIGN PATENT DOCUMENTS

| | | |
|---|---|---|
| JP | H03255139 A | 11/1991 |
| JP | 2004-224734 A | 8/2004 |
| JP | 2008214529 A | 9/2008 |
| WO | 97/02744 A1 | 1/1997 |
| WO | 98/54140 A1 | 12/1998 |
| WO | 02/080939 A2 | 10/2002 |
| WO | 02/099192 A2 | 12/2002 |
| WO | 2016/178634 A1 | 11/2016 |
| WO | 2016/186581 A1 | 11/2016 |
| WO | 2016/209732 A1 | 12/2016 |

OTHER PUBLICATIONS

Narita, et al., Effects of charge density and hydrophobicity of ionene polymer on cell binding and viability, Colloid Polym. Sci, 2000, pp. 884-887.

Mattheis, et al., Closing One of the Last Gaps in Polyionene Compositions: Alkyloxyethylammonium Ionenes as Fast-Acting Biocides, Macromolecular Bioscience, 2012, pp. 341-349, vol. 12.

Strassburg, et al., Nontoxic, Hydrophilic Cationic Polymers—Identified as Class of Antimicrobial Polymers, Macromolecular Bioscience, 2015, pp. 1710-1723, vol. 15.

Mayr, et al., Antimicrobial and Hemolytic Studies of a Series of Polycations Bearing Quaternary Ammonium Moieties: Structural and Topological Effects, International Journal of Molecular Sciences, 2017, 8 pages, vol. 18, No. 303.

Tamami, Synthesis and Characterization of Ammonium Ionenes Containing Hydrogen Bonding Functionalities, Dec. 6, 2012, 108 pages, Virginia Polytechnic Institute and State University.

Brown et al., The Structure Activity Relationship of Urea Derivatives as Anti-Tuberculosis Agents, Bioorg Med Chem. Sep. 15, 2011, pp. 5585-5595 vol. 19, No. 18.

Williams, Influence of Electrostatic Interactions and Hydrogen Bonding on the Thermal and Mechanical Properties of Step-Growth Polymers, Oct. 21, 2008, 375 pages, Virginia Polytechnic Institute and State University.

List of IBM Patents or Applications Treated as Related.

International Search Report and Written Opinion received for PCT Application Serial No. PCT/IB2018/059624 dated Apr. 17, 2019, 8 pages.

Non-Final Office Action received for U.S. Appl. No. 15/839,388 dated Jul. 10, 2019, 52 pages.

Murakami et al., "Syntheses of Macrocyclic Enzyme Models, Part 4. Preparation and Characterization of Cationic Octopus Azaparacyclophanes", Organic and Bio-Organic Chemistry, Journal of the Chemical Society, Perkin Transactions 1, Issue 11, Jan. 1, 1981, pp. 2800-2808.

Non-Final Office Action received for U.S. Appl. No. 15/839,199 dated Jun. 26, 2019, 66 pages.

Tiecco et al., "Biocidal and inhibitory activity screening of de novo synthesized surfactants against two eukaryotic and two prokaryotic microbial species", Science Direct, Colloids and Surfaces B: Biointerfaces, vol. 111, Nov. 1, 2013, 35 pages.

Non-Final Office Action received for U.S. Appl. No. 15/839,402 dated Jun. 26, 2019, 56 pages.

Odagi et al., "Origin of Stereocontrol in Guanidine-Bisurea Bifunctional Organocatalyst That Promotes α-Hydroxylation of Tetralone-Derived β-Ketoesters: Asymmetric Synthesis of β- and γ-Substituted Tetralone Derivatives via Organocatalytic Oxidative Kinetic Resolution", Journal of the American Chemical Society, Jan. 2015, pp. 1909-1915.

Magri et al., "Rethinking the old antiviral drug moroxydine: Discovery of novel analogues as anti-hepatitis C virus (HCV) agents", Bioorganic and Medicinal Chemistry Letters, vol. 25, No. 22, Nov. 2015, pp 5372-5376.

International Search Report and Written Opinion received for PCT Application Serial No. PCT/IB2018/059621 dated Apr. 10, 2019, 8 pages.

Final Office Action received for U.S. Appl. No. 15/839,199 dated Sep. 26, 2019, 25 pages.

Non-Final Office Action received for U.S. Appl. No. 15/839,270 dated Sep. 16, 2019, 70 pages.

Non-Final Office Action received for U.S. Appl. No. 15/839,397 dated Sep. 17, 2019, 47 pages.

Wettig et al., "Thermodynamic and aggregation properties of aza- and imino-substituted gemini surfactants designed for gene delivery", Physical Chemistry Chemical Physics, vol. 9, 2007, pp. 871-877.

Notice of Allowance received for U.S. Appl. No. 15/839,402 dated Oct. 24, 2019, 113 pages.

Chahboune et al., "Application of liquid chromatography/electrospray ionization tandem mass spectrometry for the elucidation of hydroxyl radical oxidation of metsulfuron methyl and related sulfonylurea pesticide products: evidence for the triazine skeleton scission", Rapid Communications in Mass Spectrometry, vol. 29, Sep. 2015, pp. 1370-1380.

Rafqah et al., "Kinetics and mechanism of the degradation of the pesticde metsulfuron methyl induced by excitation of iron(III) aqua complexes in aqueous solutions: steady state and transient absorption spectroscopy studies", Photochem. Photobial. Sci., vol. 3, 2004, pp. 296-304.

Si et al., "Leaching and degradation of ethametsulfuron-methyl in soil", Cehmosphere, vol. 60, 2005, pp. 601-609.

Li-Feng et al., "Biodegradation of Ethametsulfuron-Methyl by *Pseudomonas* sp. SW4 Isolated from Contaminated Soil", Curr Microbial, vol. 55, 2007, pp. 420-426.

Non-Final Office Action received for U.S. Appl. No. 15/839,410 dated Oct. 31, 2019, 41 pages.

Final Office Action received for U.S. Appl. No. 15/839,388 dated Dec. 5, 2019, 16 pages.

Advisory Action received for U.S. Appl. No. 15/839,199, dated Nov. 19, 2019, 16 pages.

Non-Final Office Action received for U.S. Appl. No. 15/839,199 dated Dec. 26, 2019, 156 pages.

Haque et al., "Synthesis, Characterization, and Crystal Structures of Bis-Imidazolium Salts and Respective Dinuclear Ag(I) N-Heterocyclic Carbene Complexes: In Vitro Anticancer Studies against Human Colon Cancer" and "Breast Cancer", Hindawi Publishing Corporation Journal of Chemistry, 2013, 11 pages.

Wynne et al., "Synthesis and Development of a Multifunctional Self-Decontaminating Polyurethane Coating", Applied Materials and Interfaces, 2011, pp. 2005-2011.

Oi'Khovik et al., "Synthesis, Antimicrobial and Antifungal Activity of Double Quaternary Alnmonium Salts of Biphenyls", Russian Journal of General Chemistry, vol. 83, No. 2, 2013, pp. 329-335.

Jones et al., ortlo Substitution Rearrangement vs. β-Elimination of Quaternary Ammonium Ion-Alcohols and Methyl Ether with Excess Sodium Amide[1], vol. 27 ,1962, pp. 806-814.

Menger et al., "Synthesis and Properties of Nine New Polyhydroxylated Surfactants", Langmuir, vol. 12, No. 6, 1996, pp. 1471-1473.

Final Office Action received for U.S. Appl. No. 15/839,397 dated Dec. 16, 2019, 31 pages.

Shen et al., "Synthesis of Highly Ordered Thermally Stable Cubic Mesostructured Zirconium Oxophosphate Templated by Tri-Headgroup Quaternary Ammonium Surfactants", Chem. Mater, vol. 15, No. 21, 2003, pp. 4046-4051.

Wang et al., "Transfection and structural properties of phytanyl substituted gemini surfactant-based vectors for gene delivery", Phys. Chem. Chem. Phys., 2013, vol. 15, pp. 20510-20516.

Non-Final Office Action received for U.S. Appl. No. 15/839,410 dated Apr. 22, 2020, 38 pages.

* cited by examiner

┌─────────────────────────────────────────────────────────────┐
│ POLYMERIZING A FIRST MONOMER AND A SECOND MONOMER           │
│ TO FORM AN AMINE MONOMER, THE FIRST MONOMER                 │
│ COMPRISING A MOLECULAR BACKBONE, AND THE MOLECULAR          │ ← 302
│ BACKBONE COMPRISING A NORSPERMIDINE STRUCTURE AND A         │
│ SECONDARY AMINO GROUP, WHEREIN THE POLYMERIZING             │
│ COVALENTLY BONDS THE SECOND MONOMER TO THE                  │
│ SECONDARY AMINO GROUP                                       │
└─────────────────────────────────────────────────────────────┘
                              │
                              ▼
┌─────────────────────────────────────────────────────────────┐
│ DISSOLVING THE FIRST MONOMER AND THE SECOND                 │
│ MONOMER IN A SOLVENT AT A TEMPERATURE GREATER THAN          │ ← 304
│ OR EQUAL TO 15°C AND LESS THAN OR EQUAL TO 150°C FOR A      │
│ PERIOD OF TIME GREATER THAN OR EQUAL TO 8 HOURS AND         │
│ LESS THAN OR EQUAL TO 72 HOURS                              │
└─────────────────────────────────────────────────────────────┘

┌─────────────────────────────────────────────────┐
│ DISSOLVING AN AMINE MONOMER AND AN ELECTROPHILE IN A │ ← 802
│ SOLVENT, THE AMINE MONOMER COMPRISING A MOLECULAR │
│ BACKBONE, THE MOLECULAR BACKBONE COMPRISING A │
│ NORSPERMIDINE STRUCTURE, AND A FUNCTIONAL GROUP │
│ COVALENTLY BONDED TO THE NORSPERMIDINE STRUCTURE │
└─────────────────────────────────────────────────┘
                         ↓
┌─────────────────────────────────────────────────┐
│ POLYMERIZING THE AMINE MONOMER AND THE │ ← 804
│ ELECTROPHILE TO FORM AN IONENE UNIT, THE IONENE UNIT │
│ COMPRISING A CATION DISTRIBUTED ALONG THE MOLECULAR │
│ BACKBONE, WHEREIN THE IONENE UNIT HAS ANTIMICROBIAL │
│ FUNCTIONALITY │
└─────────────────────────────────────────────────┘

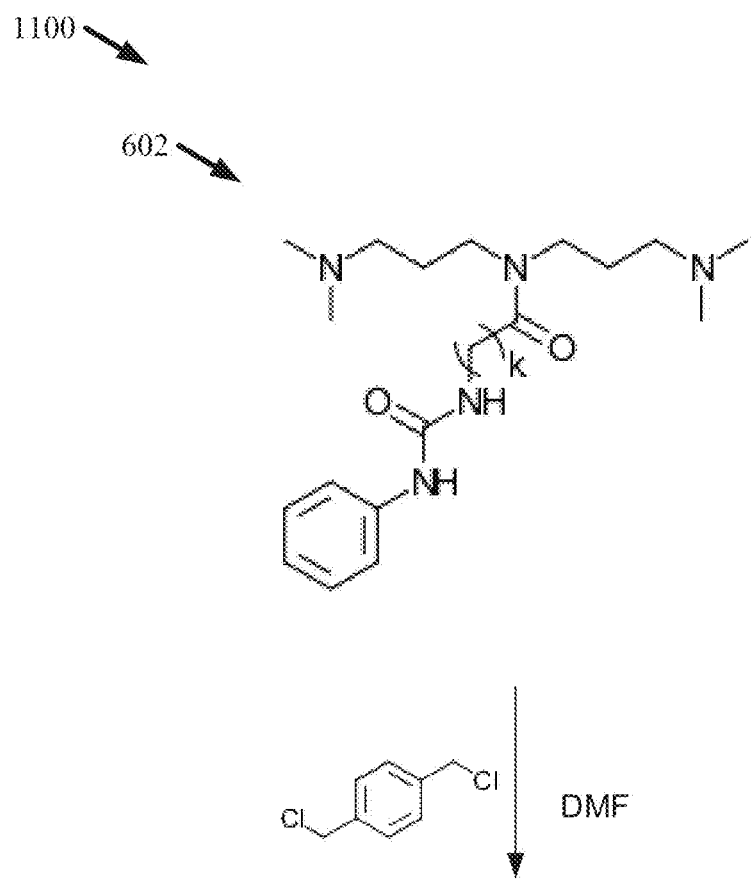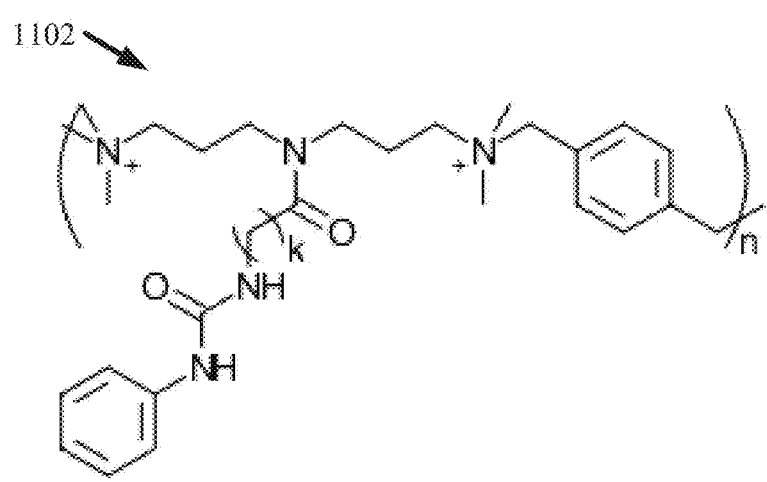
FIG. 11

1300 ↘

| R₂ | m/n Ratio | $M_{n,SEC}$ (g/mol) | Đ | SA (μg/mL) | EC (μg/mL) | PA (μg/mL) | CA (μg/mL) | Hemolysis $HC_{50}$ |
|---|---|---|---|---|---|---|---|---|
| Phenyl | 100/0 | 1,500 | 1.7 | 8 | 63 | 31 | 31 | >2000 |
| Phenyl | 50/50 | 4,500 | 2.8 | 4 | 16-31 | 31 | 16 | >2000 |
| Ethyl | 100/0 | 1,500 | 2.5 | 16 | 125 | 31 | 125 | >2000 |
| Ethyl | 50/50 | 2,800 | 2.8 | 2 | 31 | 8 | 16 | >2000 |
| Octyl | 100/0 | 3,200 | 1.9 | 4 | 16 | 8 | 16 | 31-63 |
| Octyl | 50/50 | 7,400 | 2.6 | 4 | 16 | 16 | 8 | 31-63 |
| i-Propyl | 100/0 | 2,600 | 1.8 | 16-31 | 500 | 16 | 63 | >2000 |
| i-Propyl | 50/50 | 5,900 | 2.6 | 8 | 31 | 16 | 16 | >2000 |
| s-Butyl | 100/0 | 2,300 | 2.0 | 16 | 500 | 16-31 | 125 | >2000 |
| s-Butyl | 50/50 | 5,400 | 3.2 | 5,400 | 31 | 16 | 16 | >2000 |

| K | m/n Ratio | $M_{n,SEC}$ (g/mol) | Đ | SA (µg/mL) | EC (µg/mL) | PA (µg/mL) | CA (µg/mL) | Hemolysis $HC_{50}$ |
|---|---|---|---|---|---|---|---|---|
| 3 | 100/0 | 2,100 | 3.2 | 31 | 63 | 63 | 250 | >2000 |
| 3 | 50/50 | 3,000 | 4.6 | 4 | 16 | 16 | 16 | 250 |
| 5 | 100/0 | 2,400 | 2.2 | 31 | 125 | 63 | 250 | >2000 |
| 5 | 50/50 | 2,800 | 4.1 | 16 | 31 | 16 | 31 | >2000 |

```
CONTACTING A PATHOGEN WITH A CHEMICAL COMPOUND, THE
CHEMICAL COMPOUND COMPRISING AN IONENE UNIT, THE
IONENE UNIT COMPRISING A MOLECULAR BACKBONE AND A     — 1702
CATION DISTRIBUTED ALONG THE MOLECULAR BACKBONE,
AND THE MOLECULAR BACKBONE COMPRISING A
NORSPERMIDINE STRUCTURE, WHEREIN THE IONENE UNIT HAS
ANTIMICROBIAL FUNCTIONALITY
```

```
ELECTROSTATICALLY DISRUPTING A MEMBRANE OF THE        — 1704
PATHOGEN UPON CONTACTING THE PATHOGEN WITH THE
CHEMICAL COMPOUND
```

US 10,667,514 B2

ANTIMICROBIAL IONENE COMPOSITIONS WITH A VARIETY OF FUNCTIONAL GROUPS

BACKGROUND

The subject disclosure relates to one or more ionene compositions with antimicrobial functionalities, and more specifically, to one or more amine monomers having a variety of functional groups and able to become ionenes and/or polyionenes.

SUMMARY

The following presents a summary to provide a basic understanding of one or more embodiments of the invention. This summary is not intended to identify key or critical elements, or delineate any scope of the particular embodiments or any scope of the claims. Its sole purpose is to present concepts in a simplified form as a prelude to the more detailed description that is presented later. In one or more embodiments described herein, methods and/or compositions regarding ionenes and/or polyionenes with antimicrobial functionality are described.

According to an embodiment, a monomer is provided. The monomer can comprise a molecular backbone, which can comprise a norspermidine structure. The norspermidine structure can comprise a tertiary amino group. The tertiary amino group can comprise a functional group, and an amino group of the norspermidine structure can be capable of being ionized.

According to an embodiment, a chemical compound is provided. The chemical compound can comprise an ionene unit, which can comprise a cation distributed along a molecular backbone. The molecular backbone can comprise a norspermidine structure. Also, the ionene unit can comprise a urea functional group covalently bonded to the norspermidine structure, and the ionene unit can have antimicrobial functionality.

According to an embodiment, a chemical compound is provided. The chemical compound can comprise an ionene unit, which can comprise a cation distributed along a molecular backbone. The molecular backbone can comprise a norspermidine structure. Also, the ionene unit can comprise an amide functional group covalently bonded to the norspermidine structure, and the ionene unit can have antimicrobial functionality.

According to an embodiment, a method is provided. The method can comprise polymerizing a first monomer and a second monomer to form an amine monomer. The first monomer can comprise a molecular backbone, which can comprise a norspermidine structure and a secondary amino group. The polymerizing can covalently bond the second monomer to the secondary amino group.

According to an embodiment, a method is provided. The method can comprise dissolving an amine monomer and an electrophile in a solvent. The amine monomer can comprise a molecular backbone, which can comprise a norspermidine structure. Also, a functional group can be covalently bonded to the norspermidine structure. The method can also comprise polymerizing the amine monomer and the electrophile to form an ionene unit. The ionene unit can comprise a cation distributed along the molecular backbone. Further, the ionene unit can have antimicrobial functionality.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3 illustrates a flow diagram of an example, non-limiting method that can facilitate generation of one or more amine monomers in accordance with one or more embodiments described herein.

FIG. 8 illustrates a flow diagram of an example, non-limiting method that can facilitate generation of one or more ionene units in accordance with one or more embodiments described herein.

FIG. 11 illustrates a diagram of an example, non-limiting scheme that can facilitate generation of one or more ionene compositions in accordance with one or more embodiments described herein.

FIG. 13 illustrates a diagram of an example, non-limiting chart that can depict structural characteristics and/or antimicrobial functionality of one or more ionene compositions in accordance with one or more embodiments described herein.

FIG. 14 illustrates a diagram of an example, non-limiting chart that can depict structural characteristics and/or antimicrobial functionality of one or more ionene compositions in accordance with one or more embodiments described herein.

FIG. 17 illustrates a flow diagram of an example, non-limiting method that can facilitate killing of a pathogen with one or more ionene composition in accordance with one or more embodiments described herein.

DETAILED DESCRIPTION

Figure 1A:
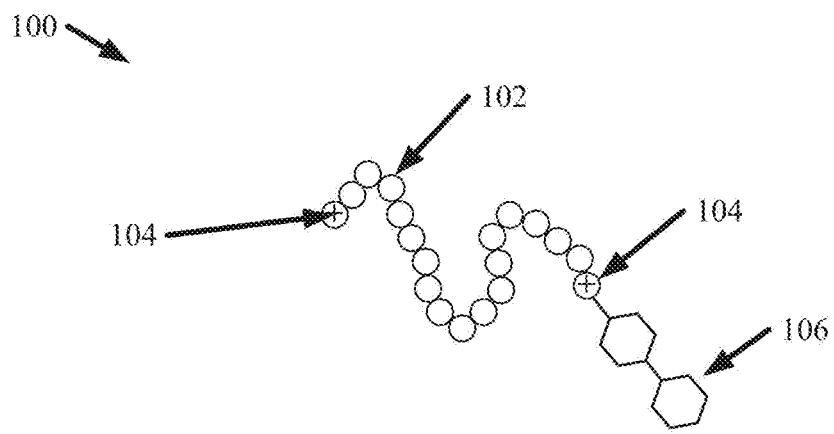
FIG. 1A illustrates a diagram of an example, non-limiting ionene unit in accordance with one or more embodiments described herein.

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

The discovery and refinement of antibiotics was one of the crowning achievements in the $20^{th}$ century that revolutionized healthcare treatment. For example, antibiotics such as penicillin, ciprofloxacin and, doxycycline can achieve microbial selectivity through targeting and disruption of a specific prokaryotic metabolism, while concurrently, remaining benign toward eukaryotic cells to afford high selectivity. If properly dosed, they could eradicate infection. Unfortunately, this therapeutic specificity of antibiotics also leads to their undoing as under-dosing (incomplete kill) allows for minor mutative changes that mitigate the effect of the antibiotic leading to resistance development. Consequently, nosocomial infections, caused by medication-resistant microbes such as methicillin-resistant *Staphylococcus aureus* (MRSA), multi-medication-resistant *Pseudomonas aeruginosa* and vancomycin-resistant Enterococci (VRE) have become more prevalent. An added complexity is the pervasive use of antimicrobial agents in self-care products, sanitizers and hospital cleaners etc, including anilide, bis-phenols, biguanides and quaternary ammonium compounds, where a major concern is the development of cross- and co-resistance with clinically used antibiotics, especially in a hospital setting. Another unfortunate feature with triclosan, for example, is its cumulative and persistent effects in the skin. Moreover, biofilms have been associated with numerous nosocomial infections and implant failure, yet the eradication of biofilms is an unmet challenge to this date. Since antibiotics are not able to penetrate through extracellular polymeric substance that encapsulates bacteria in the biofilm, further complexities exist that lead to the development of medication resistance.

However, polymers having a cationic charge can provide electrostatic disruption of the bacterial membrane interaction. Furthermore, cationic polymers are readily made amphiphilic with addition of hydrophobic regions permitting both membrane association and integration/lysis. The amphiphilic balance has shown to play an important effect not only in the antimicrobial properties but also in the hemolytic activity. Many of these antimicrobial polymers show relatively low selectivity as defined by the relative toxicity to mammalian cells or hemolysis relative to pathogens.

One design feature for said antimicrobial polymers is the installation of functional groups. Highly specific functional groups can be important to understand such properties as protein adsorption, targeting of bacteria surfaces, navigation of cellular membranes and intercellular killing of bacteria, toxicity mitigation, just to name a few. For example, tuberculosis resides primarily inside macrophages where therapeutic efficacy is predicated on the ability to navigate this barrier without loss in therapeutic efficacy. Since macrophages typically have mannose receptors on the surface, chemical compositions decorated with mannose can allow trafficking and subsequent intercellular killing. Tuberculosis is a very unique pathogen that can have a "waxy" surface with one key target that is mycolic functional group acid. Chemical compounds that do not interact with mycolic acid generally readily garner resistance. The ability of chemical compounds to target the acid group can have a marked effect on antimicrobial functionality.

The diversity of both viral and microbial pathogens presents a host of complex targets requiring general methods to install functionality on a chemical compound scaffold without the loss of efficacy. The inexpensive and commercially available amine monomer, 3,3'-iminobis(N, N-dimethyl propylamine) can functional as a good candidate as the secondary amine can be readily transformed. Various embodiments described herein can regard an amine monomer derived from 3,3'-iminobis(N, N-dimethyl propylamine), which can comprise a variety of functional groups and can be ionized with an electrophile to form one or more ionene units comprising a chemical compound. Example functional groups can include, but are not limited to: carbamate functional groups, urea functional groups, and/or amide functional groups.

As used herein, the term "ionene" can refer to a polymer unit, a copolymer unit, and/or a monomer unit that can comprise a nitrogen cation and/or a phosphorus cation distributed along, and/or located within, a molecular backbone, thereby providing a positive charge. Example nitrogen cations include, but are not limited to: quaternary ammonium cations, protonated secondary amine cations, protonated tertiary amine cations, and/or imidazolium cations. Example, phosphorus cations include, but are not limited to: quaternary phosphonium cations, protonated secondary phosphine cations, and protonated tertiary phosphine cations. As used herein, the term "molecular backbone" can refer to a central chain of covalently bonded atoms that form the primary structure of a molecule. In various embodiments described herein, side chains can be formed by bonding one or more functional groups to a molecular backbone. As used herein, the term "polyionene" can refer to a polymer that can comprise a plurality of ionenes. For example, a polyionene can comprise a repeating ionene.

FIG. 1A illustrates a diagram of an example, non-limiting ionene unit 100 in accordance with one or more embodiments described herein. The ionene unit 100 can comprise a molecular backbone 102, one or more cations 104, and/or one or more hydrophobic functional groups 106. In various embodiments, an ionene and/or a polyionene described herein can comprise the ionene unit 100. For example, a polyionene described herein can comprise a plurality of ionenes bonded together, wherein the bonded ionenes can have a composition exemplified by ionene unit 100.

Figure 1B:
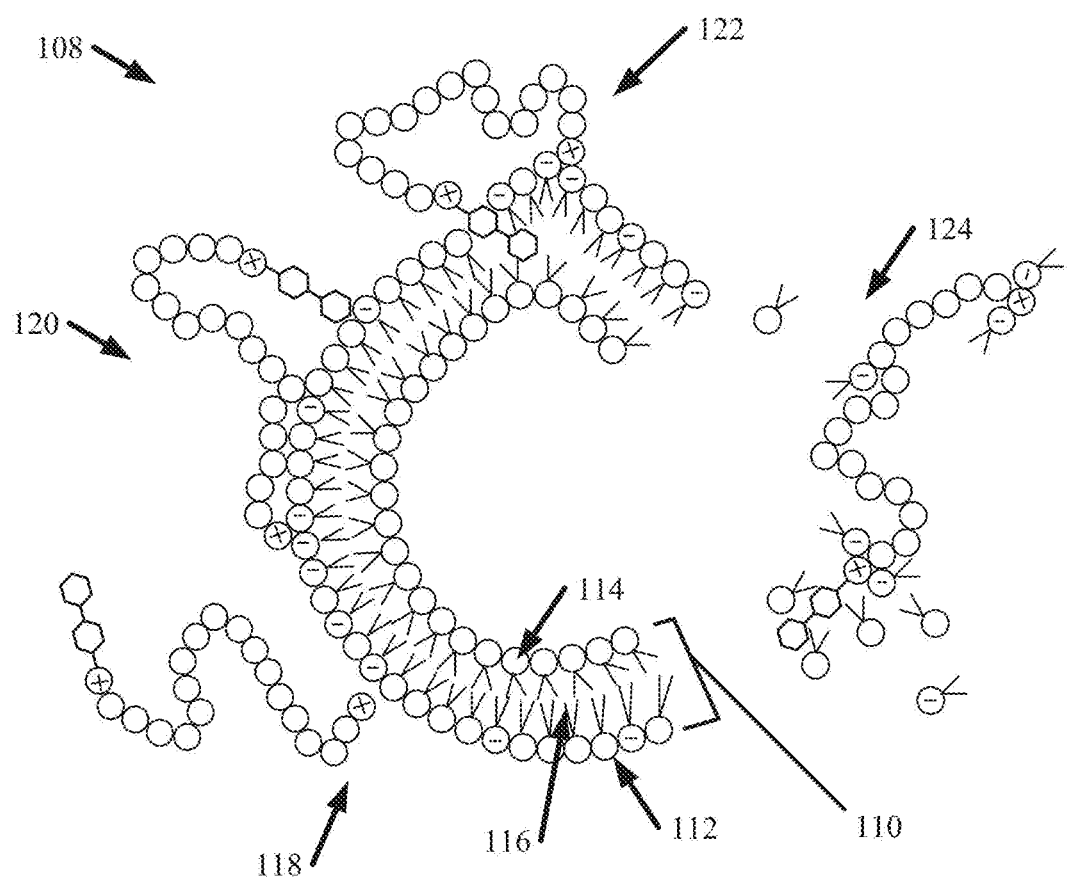
FIG. 1B illustrates a diagram of an example, non-limiting lysis process that can be performed by one or more ionene units in accordance with one or more embodiments described herein.

The molecular backbone 102 can comprise a plurality of covalently bonded atoms (illustrated as circles in FIGS. 1A and 1B). The atoms can be bonded in any desirable formation, including, but not limited to: chain formations, ring formations, and/or a combination thereof. The molecular backbone 102 can comprise one or more chemical structures including, but not limited to: alkyl structures, aryl structures, alkane structures, aldehyde structures, ester structures, carboxyl structures, carbonyl structures, amine structures, amide structures, phosphide structures, phosphine structures, a combination thereof, and/or the like. One of ordinary skill in the art will recognize that the number of atoms that can comprise the molecular backbone can vary depending of the desired function of the ionene unit 100. For example, while nineteen atoms are illustrated in FIG. 1A, a molecular backbone 102 that can comprise dozens, hundreds, and/or thousands of atoms is also envisaged.

Located within the molecular backbone 102 are one or more cations 104. As described above, the one or more cations 104 can comprise nitrogen cations and/or phosphorous cations. The cations 104 can be distributed along the molecular backbone 102, covalently bonded to other atoms within the molecular backbone 102. In various embodiments, the one or more cations 104 can comprise at least a portion of the molecular backbone 102. One of ordinary skill in the art will recognize that the number of a cations 104 that can comprise the ionene unit 100 can vary depending of the desired function of the ionene unit 100. For example, while two cations 104 are illustrated in FIG. 1A, an ionene unit 100 that can comprise dozens, hundreds, and/or thousands of cations 104 is also envisaged. Further, while FIG. 1A illustrates a plurality of cations 104 evenly spaced apart, other configurations wherein the cations 104 are not evenly spaced apart are also envisaged. Also, the one or more cations 104 can be located at respective ends of the molecular backbone 102 and/or at intermediate portions of the molecular backbone 102, between two or more ends of the molecular backbone 102. The one or more cations 104 can provide a positive charge to one or more locations of the ionene unit 100.

The one or more hydrophobic functional groups 106 can be bonded to the molecular backbone 102 to form a side chain. The one or more of the hydrophobic functional groups 106 can be attached to the molecular backbone 102 via bonding with a cation 104. Additionally, one or more hydrophobic functional groups 106 can be bonded to an electrically neutral atom of the molecular backbone 102. The ionene unit 100 can comprise one or more hydrophobic functional groups 106 bonded to: one or more ends of the molecular backbone 102, all ends of the molecular backbone 102, an intermediate portion (e.g., a portion between two ends) of the molecular backbone 102, and/or a combination thereof.

While a biphenyl group is illustrated in FIG. 1A as the hydrophobic functional group 106, other functional groups that are hydrophobic are also envisaged. Example, hydrophobic functional groups 106 can include, but are not limited to: alkyl structures, aryl structures, alkane structures, aldehyde structures, ester structures, carboxyl structures, carbonyl structures, carbonate structures, alcohol structures, a combination thereof, and/or the like. In various embodiments, the one or more hydrophobic functional groups 106 can comprise the same structure. In other embodiments, one or more of the hydrophobic functional groups 106 can comprise a first structure and one or more other hydrophobic functional groups 106 can comprise another structure.

FIG. 1B illustrates a diagram of an example, non-limiting lysis process 108 that can be facilitated by the ionene unit 100 in accordance with one or more embodiments described herein. Repetitive description of like elements employed in other embodiments described herein is omitted for sake of brevity. The lysis process 108 can comprise a plurality of stages, which can collectively comprise an attack mechanism that can be performed by the ionene unit 100 against a pathogen cell. Example pathogen cells can include, but are not limited to: Gram-positive bacteria cells, Gram-negative bacteria cells, fungi cells, and/or yeast cells.

The target pathogen cell can comprise a membrane having a phospholipid bilayer 110. In various embodiments, the membrane can be an extracellular matrix. The phospholipid bilayer 110 can comprise a plurality of membrane molecules 112 covalently bonded together, and the membrane molecules 112 can comprise a hydrophilic head 114 and one or more hydrophobic tails 116. Further, one or more of the plurality of membrane molecules 112 can be negatively charged (as illustrated in FIG. 1B with a "-" symbol).

At 118, electrostatic interaction can occur between the positively charged cations 104 of the ionene unit 100 and one or more negatively charged membrane molecules 112. For example, the negative charge of one or more membrane molecules 112 can attract the ionene unit 100 towards the membrane (e.g., the phospholipid bilayer 110). Also, the electrostatic interaction can electrostatically disrupt the integrity of the membrane (e.g., phospholipid bilayer 110). Once the ionene unit 100 has been attracted to the membrane (e.g., phospholipid bilayer 110), hydrophobic membrane integration can occur at 120. For example, at 120 one or more hydrophobic functional groups 106 of the ionene unit 100 can begin to integrate themselves into the phospholipid bilayer 110. While the positively charged portions of the ionene unit 100 are attracted, and electrostatically disrupting, one or more negatively charged membrane molecules 112 (e.g., one or more hydrophilic heads 114), the one or more hydrophobic functional groups 106 can insert themselves between the hydrophilic heads 114 to enter a hydrophobic region created by the plurality of hydrophobic tails 116.

As a result of the mechanisms occurring at 118 and/or 120, destabilization of the membrane (e.g., the phospholipid bilayer 110) can occur at 122. For example, the one or more hydrophobic functional groups 106 can serve to cleave one or more negatively charged membrane molecules 112 from adjacent membrane molecules 112, and the positively charged ionene unit 100 can move the cleaved membrane segment (e.g., that can comprise one or more negatively charged membrane molecules 112 and/or one or more neutral membrane molecules 112 constituting a layer of the phospholipid bilayer 110) away from adjacent segments of the membrane (e.g., adjacent segments of the phospholipid bilayer 110). As cleaved segments of the membrane (e.g., the phospholipid bilayer 110) are pulled away, they can fully detach from other membrane molecules 112 at 124, thereby forming gaps in the membrane (e.g., the phospholipid bilayer 110). The formed gaps can contribute to lysis of the subject pathogen cell. In various embodiments, a plurality of ionene units 100 can perform the lysis process 108 on a cell simultaneously. Furthermore, the ionene units 100 participating in a lysis process 108 need not perform the same stages of the attack mechanism at the same time.

Figure 2:
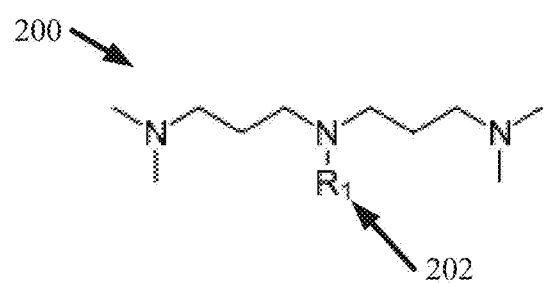
FIG. 2 illustrates a diagram of an example, non-limiting chemical formula that can characterize one or more amine monomers in accordance with one or more embodiments described herein.

FIG. 2 illustrates a diagram of an example, non-limiting chemical formula 200 that can characterize one or more amine monomers in accordance with one or more embodiments described herein. Repetitive description of like elements employed in other embodiments described herein is omitted for sake of brevity. The one or more amine monomers that can be characterized by chemical formula 200 can undergo one or more polymerizations to form one or more ionene units 100 in accordance with one or more embodiments herein.

The one or more amine monomers that can be characterized by chemical formula 200 can comprise a molecular backbone 102. The molecular backbone 102 can comprise one or more norspermidine structures. For example, the molecular backbone 102 can comprise three or more amino groups. The amino groups can comprise primary amino groups, secondary amino groups, tertiary amino groups, and/or heterocyclic groups (e.g., imidazole groups and/or pyridine groups). Further, each amino group comprising the molecular backbone 102 can have varying structures. Moreover, one or more of the amino groups comprising the one or more norspermidine structures can be capable of being ionized (e.g., via an alkylation process and/or a quaternization process).

As shown in FIG. 2, one or more of the amine monomers that can be characterized by chemical formula 200 can comprise three tertiary amino groups. In one or more embodiments, one or more of the amine monomers that can be characterized by chemical formula 200 can be derived from 3,3'-iminobis(N, N-dimethyl propylamine). However, in various embodiments, one or more of the amine monomers that can be characterized by chemical formula 200 can be derived from a molecule other than 3,3'-iminobis(N, N-dimethyl propylamine).

The one or more amine monomers that can be characterized by chemical formula 200 can comprise one or more functional groups 202. As shown in FIG. 2, "$R_1$" can represent the one or more functional groups 202. The one or more functional groups 202 can be covalently bonded to the one or more norspermidine structures. For example, the one or more functional groups 202 can comprise one or more of the amino groups of the one or more norspermidine structures (e.g., as shown in FIG. 2). The one or more functional groups 202 can comprise, for example, carbamate functional groups, urea functional groups, amide functional groups, a combination thereof, and/or the like.

For example, the one or more functional groups 202 can comprise one or more carbamate functional groups. The one or more carbamate functional groups can be derived from one or more carbonates (e.g., cyclic carbonates). The one or more carbamate functional groups can comprise alkyl structures and/or aryl structures. Additionally, the one or more carbamate functional groups can comprise additional functional groups such as, but not limited to: hydroxyl groups, amino groups, amide groups, ester groups, ether groups, ketone groups, carbonyl groups, alkenyl groups, carboxyl groups, mannose groups, urea groups, a combination thereof, and/or the like.

In another example, the one or more functional groups 202 can comprise one or more urea functional groups. The one or more urea functional groups can be derived from one or more cyanates (e.g., isocyanates). The one or more urea functional groups can comprise alkyl and/or aryl structures. Additionally, the one or more urea functional groups can comprise additional functional groups such as, but not limited to: phenyl structures, ethyl structures, octyl structures, propyl structures, butyl structures, a combination thereof, and/or the like.

In a further example, the one or more functional groups 202 can comprise one or more amide functional groups. The one or more amide functional groups can be derived from one or more acid compounds. The one or more amide functional groups can comprise alkyl structures and/or aryl structures. Additionally, the one or more amide functional groups can comprise additional functional groups such as, but not limited to: amino groups, amide groups, ester groups, ether groups, ketone groups, carbonyl groups, alkenyl groups, carboxyl groups, urea groups, a combination thereof, and/or the like.

FIG. 3 illustrates a flow diagram of an example, non-limiting method 300 that can facilitate generating one or more amine monomers that can be characterized by chemical formula 200 in accordance with one or more embodiments described herein. Repetitive description of like elements employed in other embodiments described herein is omitted for sake of brevity.

At 302, the method 300 can comprise polymerizing one or more first monomers and one or more second monomers to form one or more amine monomers (e.g., that can be characterized by chemical formula 200). The one or more first monomers can comprise a molecular backbone 102, which can comprise one or more norspermidine structures. For example, the molecular backbone 102 can comprise three or more amino groups. The amino groups can comprise primary amino groups, secondary amino groups, tertiary amino groups, and/or heterocyclic groups (e.g., imidazole groups and/or pyridine groups). Further, each amino group comprising the molecular backbone 102 can have varying structures. For example, the molecular backbone 102 (e.g., the one or more norspermidine structures) can comprise one or more secondary amino groups and/or one or more tertiary amino groups. Moreover, one or more of the amino groups comprising the one or more norspermidine structures can be capable of being ionized (e.g., via an alkylation process and/or a quaternization process). In one or more embodiments, one or more of the first monomers can be 3,3'-iminobis(N, N-dimethyl propylamine). However, in various embodiments, one or more of the first monomers can be one or more molecules other than 3,3'-iminobis(N, N-dimethyl propylamine).

Example one or more second monomers can include, but are not limited to: carbonates (e.g., cyclic carbonates), cyanates (e.g., isocyanates), acids, a combination thereof, and/or the like. For example, the one or more second monomers can comprise one or more carbonates, which can have alkyl structures and/or aryl structures that can include, but are not limited to: hydroxyl groups, amino groups, amide groups, ester groups, ether groups, ketone groups, carbonyl groups, alkenyl groups, carboxyl groups, mannose groups, urea groups, a combination thereof, and/or the like. In another example, the one or more second monomers can comprise one or more cyanates, which can have alkyl and/or aryl structures that can include, but are not limited to: phenyl structures, ethyl structures, octyl structures, propyl structures, butyl structures, a combination thereof, and/or the like. In a further example, the one or more second monomers can comprise one or more acids, which can have alkyl structures and/or aryl structures that can include, but are not limited to: amino groups, amide groups, ester groups, ether groups, ketone groups, carbonyl groups, alkenyl groups, carboxyl groups, urea groups, a combination thereof, and/or the like.

The polymerizing at 302 can covalently bond the one or more second monomers to one or more amino groups of the one or more first monomers. For example, the polymerizing at 302 can bond the one or more second monomers to one or more secondary amino groups of the one or more norspermidine structures. The polymerization at 302 can comprise subjecting one or more amino groups of the one or more first monomers to an alkylation process with the one or more second monomers.

In various embodiments, the polymerization at 302 can comprise a ring-opening polymerization (ROP). For example, the polymerization at 302 can comprise a ROP that bonds a cyclic carbonate to the one or more amino groups (e.g., one or more secondary amino groups) of the one or more first monomer's norspermidine structures. In one or more embodiments, the polymerization at 302 can comprise coupling N,N'-dicyclohexlcarbodiimide (DCC) and/or an acid with the one or more first monomers to bond one or more amide functional groups to one or more amino groups comprising one or more norspermidine structures.

At 304, the method 300 can optionally comprise dissolving the one or more first monomers and the one or more second monomers in a solvent. The solvent can be an organic solvent. Additionally, the solvent can be an aprotic solvent, a dipolar solvent, and/or an alcohol. Example solvents can include but are not limited to: dimethyl formamide (DMF), methanol, tetrahydrofuran (THF), dichloromethane (DCM), a combination thereof, and/or the like. To facilitate the dissolving, the method 300 can further comprise stirring one or more first monomers, the one or more second monomers, and/or the solvent at a temperature greater than or equal to 15 degrees Celsius (° C.) and less than or equal to 150° C. for a period of time greater than or equal to 8 hours and less than or equal to 72 hours (e.g., greater than or equal to 12 hours and less than or equal to 24 hours).

Figure 4:
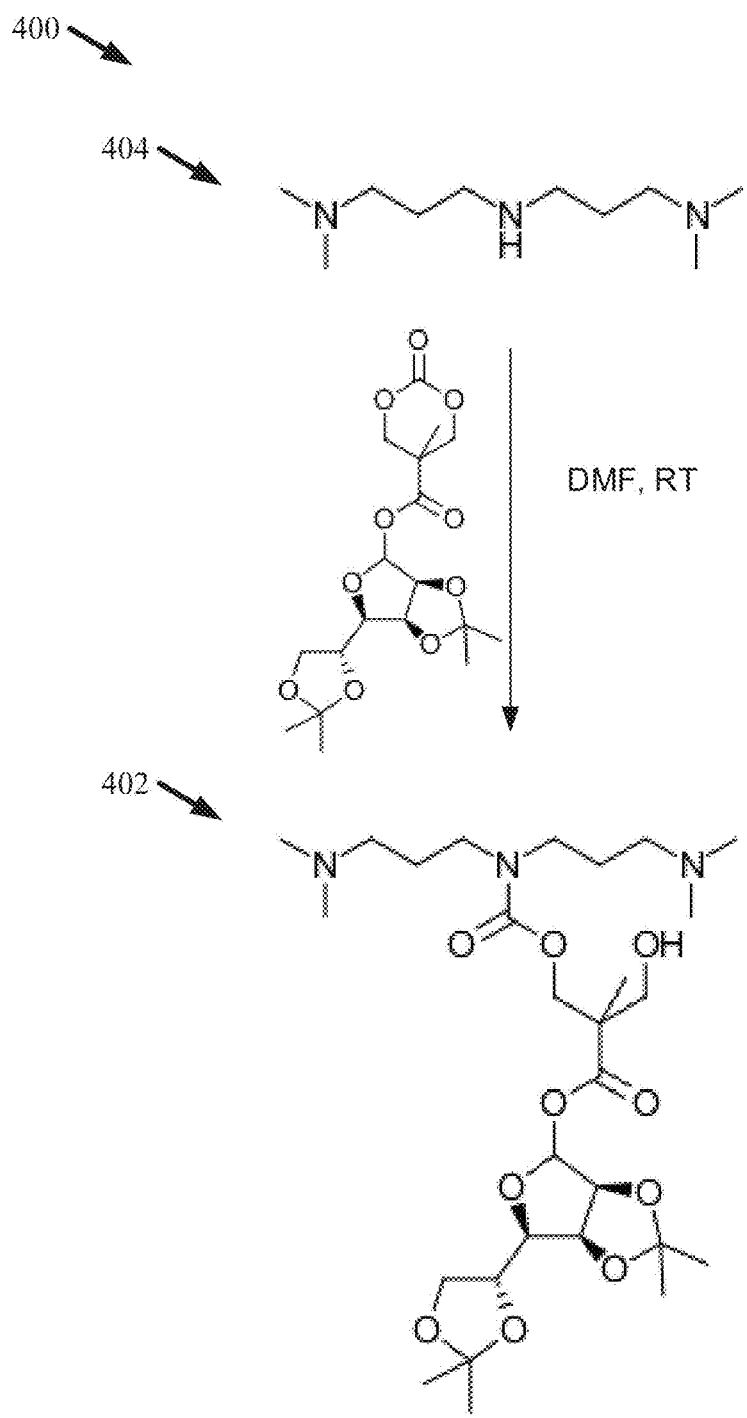
FIG. 4 illustrates a diagram of an example, non-limiting scheme that can facilitate generation of one or more amine monomers in accordance with one or more embodiments described herein.

FIG. 4 can illustrate an example, non-limiting scheme 400 that can depict the generation of one or more amine monomers (e.g., first amine monomer 402, which can be characterized by chemical formula 200) in accordance with one or more embodiments described herein (e.g., method 300). Repetitive description of like elements employed in other embodiments described herein is omitted for sake of brevity. Thus, scheme 400 can depict a generation of one or more amine monomers (e.g., first amine monomer 402, which can be characterized by chemical formula 200) in accordance with the various features of method 300. While one or more particular amine reactants (e.g., amine monomer reactant 404), second monomers, carbonates, and/or solvents are depicted; additional embodiments of scheme 400 are also envisaged. For example, the principal mechanisms of scheme 400 can be applied to any amine reactant (e.g., comprising one or more norspermidine structures), second monomers, carbonates, and/or solvents in accordance with the various features described herein (e.g., with reference to chemical formula 200 and/or method 300).

As shown in FIG. 4, scheme 400 can depict a polymerization (e.g., in accordance with method 300) of one or more amine monomer reactants 404 (e.g., 3,3'-iminobis(N, N-dimethyl propylamine)) with one or more second monomers (e.g., one or more cyclic carbonates) to generate one or more amine monomers (e.g., first amine monomer 402, which can be characterized by chemical formula 200). For example, the one or more amine monomer reactants 404 (e.g., 3,3'-iminobis(N, N-dimethyl propylamine)) can be dissolved with the one or more second monomers (e.g., one or more cyclic carbonates) in a solvent (e.g., DMF). The one or more amine monomer reactants 404 (e.g., 3,3'-iminobis(N, N-dimethyl propylamine)), the one or more second monomers (e.g., one or more cyclic carbonates), and/or the solvent (e.g., DMF) can be stirred at a temperature greater than or equal to 15° C. and less than or equal to 150° C. (e.g., room temperature ("RT")) for a period of time greater than or equal to 8 hours and less than or equal to 72 hours (e.g., greater than or equal to 12 hours and less than or equal to 24 hours).

The one or more amine monomers (e.g., first amine monomer 402, which can be characterized by chemical formula 200) can comprise a molecular backbone 102 having one or more norspermidine structures bonded to a functional group 202 (e.g., a carbamate functional group). A polymerization (e.g., the polymerization at 302) can bond the one or more second monomers (e.g., one or more cyclic carbonates) to the one or more amine monomer reactants 404 to form the one or more amine monomers (e.g., first amine monomer 402). For example, the polymerization (e.g., the polymerization at 302) can comprise a ROP that can facilitate an alkylation of one or more amino group (e.g., one or more secondary amino groups) of the one or more norspermidine structures comprising the one or more amine monomer reactants 404. Thus, the one or more amine monomers generated in accordance with scheme 400 (e.g., first amine monomer 402) can comprise the various features characterized by chemical formula 200 and can be generated in accordance with the various features of method 300.

Figure 5:
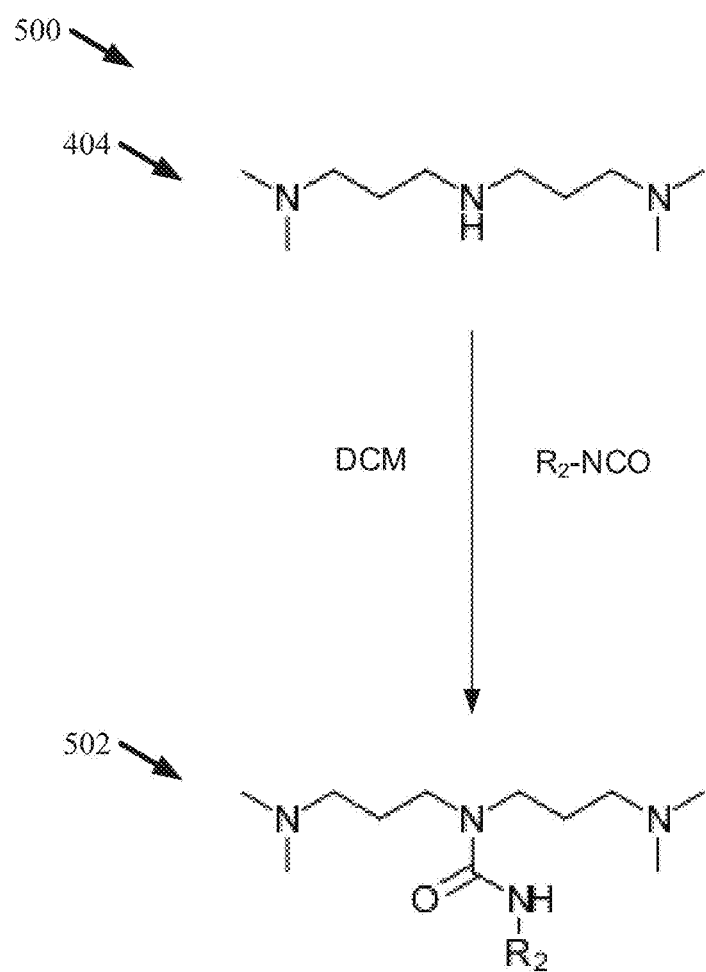
FIG. 5 illustrates a diagram of an example, non-limiting scheme that can facilitate generation of one or more amine monomers in accordance with one or more embodiments described herein.

FIG. 5 can illustrate an example, non-limiting scheme 500 that can depict the generation of one or more amine monomers (e.g., second amine monomer 502, which can be characterized by chemical formula 200) in accordance with one or more embodiments described herein (e.g., method 300). Repetitive description of like elements employed in other embodiments described herein is omitted for sake of brevity. Thus, scheme 500 can depict a generation of one or more amine monomers (e.g., second amine monomer 502, which can be characterized by chemical formula 200) in accordance with the various features of method 300. While one or more particular amine reactants (e.g., amine monomer reactant 404), second monomers, cyanates, and/or solvents are depicted; additional embodiments of scheme 500 are also envisaged. For example, the principal mechanisms of scheme 500 can be applied to any amine reactant (e.g., comprising one or more norspermidine structures), second monomers, cyanates, and/or solvents in accordance with the various features described herein (e.g., with reference to chemical formula 200 and/or method 300).

As shown in FIG. 5, scheme 500 can depict a polymerization (e.g., in accordance with method 300) of one or more amine monomer reactants 404 (e.g., 3,3'-iminobis(N, N-dimethyl propylamine)) with one or more second monomers (e.g., one or more cyanates) to generate one or more amine monomers (e.g., second amine monomer 502, which can be characterized by chemical formula 200). The one or more second monomers (e.g., one or more cyanates) can comprise one or more functional groups, represented in scheme 500 as "$R_2$." Example, functional groups of the one or more second monomers (e.g., one or more cyanates) can include, but are not limited to: phenyl groups, ethyl groups, octyl groups, propyl groups, butyl groups, a combination thereof, and/or the like.

For example, the one or more amine monomer reactants 404 (e.g., 3,3'-iminobis(N, N-dimethyl propylamine)) can be dissolved with the one or more second monomers (e.g., one or more cyanates) in a solvent (e.g., DCM). The one or more amine monomer reactants 404 (e.g., 3,3'-iminobis(N, N-dimethyl propylamine)), the one or more second monomers (e.g., one or more cyanates), and/or the solvent (e.g., DCM) can be stirred at a temperature greater than or equal to 15° C. and less than or equal to 150° C. (e.g., RT) for a period of time greater than or equal to 8 hours and less than or equal to 72 hours (e.g., greater than or equal to 12 hours and less than or equal to 24 hours).

The one or more amine monomers (e.g., second amine monomer 502, which can be characterized by chemical formula 200) can comprise a molecular backbone 102 having one or more norspermidine structures bonded to a functional group 202 (e.g., a urea functional group). A polymerization (e.g., the polymerization at 302) can bond the one or more second monomers (e.g., one or more cyanates) to the one or more amine monomer reactants 404 to form the one or more amine monomers (e.g., second amine monomer 502). For example, the polymerization (e.g., the polymerization at 302) can comprise an alkylation of one or more amino groups (e.g., one or more secondary amino groups) of the one or more norspermidine structures comprising the one or more amine monomer reactants 404. Thus, the one or more amine monomers generated in accordance with scheme 500 (e.g., second amine monomer 502) can comprise the various features characterized by chemical formula 200 and can be generated in accordance with the various features of method 300.

Figure 6:
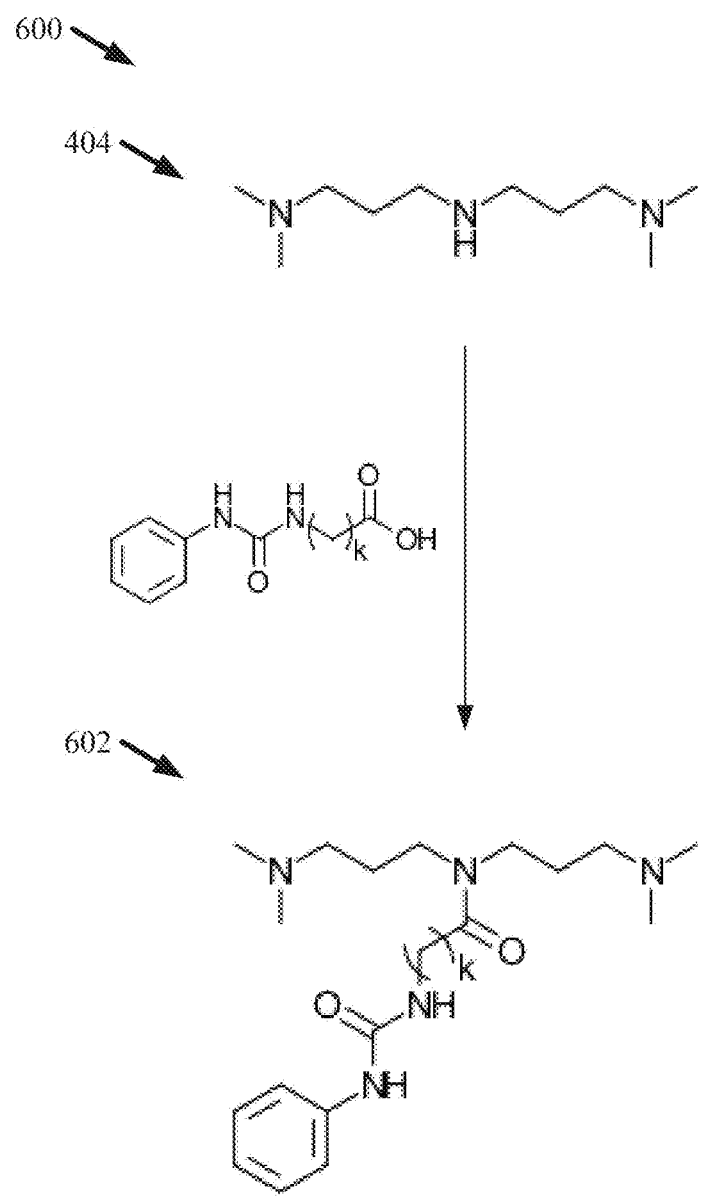
FIG. 6 illustrates a diagram of an example, non-limiting scheme that can facilitate generation of one or more amine monomers in accordance with one or more embodiments described herein.

FIG. 6 can illustrate an example, non-limiting scheme 600 that can depict the generation of one or more amine monomers (e.g., third amine monomer 602, which can be characterized by chemical formula 200) in accordance with one or more embodiments described herein (e.g., method 300). Repetitive description of like elements employed in other embodiments described herein is omitted for sake of brevity. Thus, scheme 600 can depict a generation of one or more amine monomers (e.g., third amine monomer 602, which can be characterized by chemical formula 200) in accordance with the various features of method 300. While one or more particular amine reactants (e.g., amine monomer reactant 404), second monomers, acids, and/or solvents are depicted; additional embodiments of scheme 600 are also envisaged. For example, the principal mechanisms of scheme 600 can be applied to any amine reactant (e.g., comprising one or more norspermidine structures), second monomers, acids, and/or solvents in accordance with the various features described herein (e.g., with reference to chemical formula 200 and/or method 300).

As shown in FIG. 6, scheme 600 can depict a polymerization (e.g., in accordance with method 300) of one or more amine monomer reactants 404 (e.g., 3,3'-iminobis(N, N-dimethyl propylamine)) with one or more second monomers (e.g., one or more acids) to generate one or more amine monomers (e.g., third amine monomer 602, which can be characterized by chemical formula 200). For example, the one or more amine monomer reactants 404 (e.g., 3,3'-iminobis(N, N-dimethyl propylamine)) can be dissolved with the one or more second monomers (e.g., one or more acids) in a solvent (e.g., DMF). The one or more amine monomer reactants 404 (e.g., 3,3'-iminobis(N, N-dimethyl propylamine)), the one or more second monomers (e.g., one or more acids), and/or the solvent (e.g., DMF) can be stirred at a temperature greater than or equal to 15° C. and less than or equal to 150° C. (e.g., room temperature (RT)) for a period of time greater than or equal to 8 hours and less than or equal to 72 hours (e.g., greater than or equal to 12 hours and less than or equal to 24 hours).

The one or more amine monomers (e.g., first amine monomer 402, which can be characterized by chemical formula 200) can comprise a molecular backbone 102 having one or more norspermidine structures bonded to a functional group 202 (e.g., an amide functional group). A polymerization (e.g., the polymerization at 302) can bond the one or more second monomers (e.g., one or more acids) to the one or more amine monomer reactants 404 (e.g., via replacement of one or more hydroxyl groups) to form the one or more amine monomers (e.g., third amine monomer 602). For example, the polymerization (e.g., the polymerization at 302) can comprise an alkylation of one or more amino groups (e.g., one or more secondary amino groups) of the one or more norspermidine structures comprising the one or more amine monomer reactants 404. Thus, the one or more amine monomers generated in accordance with scheme 600 (e.g., third amine monomer 602) can comprise the various features characterized by chemical formula 200 and can be generated in accordance with the various features of method 300.

Figure 7:
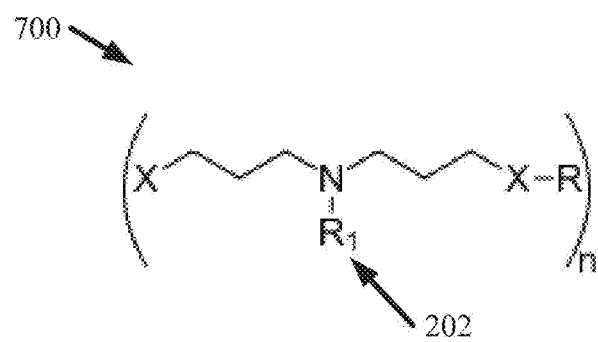
FIG. 7 illustrates a diagram of an example, non-limiting chemical formula that can characterize one or more ionene units in accordance with one or more embodiments described herein.

FIG. 7 illustrates a diagram of an example, non-limiting chemical formula 700 that can characterize the structure of an ionene unit 100 in accordance with one or more embodiments described herein. Repetitive description of like elements employed in other embodiments described herein is omitted for sake of brevity. In one or more embodiments, the ionene unit 100 characterized by chemical formula 700 can form a monomer. In various embodiments, a plurality of ionene units 100 characterized by chemical formula 700 can be covalently bond together to form a polymer (e.g., an alternating copolymer and/or a random copolymer).

As shown in FIG. 7, an ionene unit 100 characterized by chemical formula 700 can comprise a molecular backbone 102. Further, the molecular backbone 102 can comprise one or more norspermidine structures. In various embodiments, the ionene unit 100 characterized by chemical formula 700 can be derived from 3,3'-iminobis(N, N-dimethyl propylamine), wherein the one or more norspermidine structures can be derived from the 3,3'-iminobis(N, N-dimethyl propylamine). However, one or more embodiments of chemical formula 700 can comprise one or more norspermidine structures derived from one or more molecules other than 3,3'-iminobis(N, N-dimethyl propylamine).

The "X" in FIG. 7 can represent the one or more cations 104. For example, "X" can represent one or more cations 104 selected from a group that can include, but is not limited to: one or more nitrogen cations, one or more phosphorus cations, and/or a combination thereof. For instance, "X" can represent one or more nitrogen cations selected from a group that can include, but is not limited to: one or more protonated secondary amine cations, one or more protonated tertiary amine cations, one or more quaternary ammonium cations, one or more imidazolium cations, and/or a combination thereof. In another instance, "X" can represent one or more phosphorus cations selected from a group that can include, but is not limited to: one or more protonated secondary phosphine cations, one or more protonated tertiary phosphine cations, one or more quaternary phosphonium cations, and/or a combination thereof.

The one or more cations 104 (e.g., represented by "X" in chemical formula 700) can be comprise the molecular backbone 102. As shown in FIG. 7, in various embodiments, an ionene unit 100 characterized by chemical formula 700 can comprise cations 104 (e.g., represented by "X") at a plurality of locations along the molecular backbone 102. For example, cations 104 can be located at either end of the molecular backbone 102 (e.g., as illustrated in FIG. 7). However, in one or more embodiments of chemical formula 700, the molecular backbone 102 can comprise less or more cations 104 than the two illustrated in FIG. 7.

Further, the "R" shown in FIG. 7 can represent the one or more hydrophobic functional groups 106 in accordance with the various embodiments described herein. For example, the one or more hydrophobic functional groups 106 can comprise one or more alkyl groups and/or one or more aryl groups. For instance, the hydrophobic functional group 106 can be derived from one or more dialkyl halides. The one or more hydrophobic functional groups 106 (e.g., represented by "R" in FIG. 7) can be covalently bonded to one or more of the cations 104 (e.g., represented by "X" in FIG. 7) and/or the molecular backbone 102, which can comprise the one or more cations 104 (e.g., represented by "X" in FIG. 7), and/or one or more norspermidine structures.

In additional, the one or more ionene units 100 that can be characterized by chemical formula 700 can comprise one or more functional groups 202, represented in by "$R_1$" in FIG. 7. The one or more functional groups 202 comprising chemical formula 700 can comprise all the features described herein regarding the one or more functional groups 202 comprising chemical formula 200. For example, the one or more functional groups 202 comprising one or more ionene units 100 characterized by chemical formula 700 can include, but are not limited to: carbamate functional groups, urea functional groups, amide functional groups, a combination thereof, and/or the like.

Moreover, an ionene and/or polyionene characterized by chemical formula 700 can comprise a single ionene unit 100 or a repeating ionene unit 100. For example, the "n" shown in FIG. 7 can represent a first integer greater than or equal to one and less than or equal to one thousand. Thus, an ionene unit 100 characterized by chemical formula 700 can form monomers and/or polymers (e.g., alternating copolymers and/or random copolymers).

FIG. 8 illustrates another flow diagram of an example, non-limiting method 800 that can generate one or more ionene units 100, which can be characterized by chemical formula 700, in accordance with one or more embodiments described herein. Repetitive description of like elements employed in other embodiments described herein is omitted for sake of brevity. The one or more ionene units 100 generated by method 800 can be characterized by chemical formula 700 and can form monomers and/or polymers (e.g., homopolymers, alternating copolymers, and/or random copolymers).

At 802, the method 800 can comprise dissolving one or more amine monomers (e.g., characterized by chemical formula 200) with one or more electrophiles in a solvent. The one or more amine monomers (e.g., characterized by chemical formula 200) can comprise a molecular backbone 102 that has one or more norspermidine structures. The one or more amine monomers can also comprise one or more functional groups 202 (e.g., carbamate functional groups, urea functional groups, and/or amide functional groups) bonded to the one or more norspermidine structures. For example, the one or more amine monomers can be characterized by chemical formula 200 and/or generated by method 300. For instance, the one or more amine monomers can comprise first amine monomer 402 depicted in FIG. 4, second amine monomer 502 depicted in FIG. 5, and/or third amine monomer 602 depicted in FIG. 6. In one or more embodiments, the one or more amine monomers (e.g., characterized by chemical formula 200) can be prepared using one or more techniques other than those described regarding method 300.

The one or more electrophiles can comprise, for example, one or more alkyl halides (e.g., dialkyl halides). For instance, the one or more electrophiles can comprise one or more dialkyl halides having chloride and/or bromide. Example electrophiles can include, but are not are not limited to: p-xylylene dichloride, 4,4'-bis(chloromethyl)biphenyl; 1,4-bis(bromomethyl)benzene; 4,4'-bis(bromomethyl)biphenyl; 1,4-bis(iodomethyl)benzene; 1,6-dibromohexane; 1,8-dibromooctane; 1,12-dibromododecane; 1,6-dichlorohexane; 1,8-dichlorooctane; a combination thereof; and/or the like.

The solvent can be an organic solvent. Additionally, the solvent can be an aprotic solvent, a dipolar solvent, and/or an alcohol. Example solvents can include but are not limited to: DMF, methanol, a combination thereof, and/or the like. For example, DMF can be used as the solvent as it can dissolve the reactants at elevated temperatures. In one or more embodiments, equimolar amounts of the plurality of degradable amine monomers and the one or more electrophiles can be dissolved in the solvent.

To facilitate the dissolving at 802, the method 800 can optionally comprise stirring the one or more amine monomers, the one or more electrophiles, and the solvent at a temperature greater than or equal to 15° C. and less than or equal to 150° C. for a period of time greater than or equal to 8 hours and less than or equal to 72 hours (e.g., greater than or equal to 12 hours and less than or equal to 24 hours). Additionally, an organocatalyst can optionally be added at 802. Example organocatalysts include, but are not limited to: 1,8-diazabicyclo[5.4.0]undec-7-ene ("DBU"), 1-(3,5-bis(trifluoromethyl)-phenyl)-3-cyclohexyl-2-thiourea ("TU"), a combination thereof, and/or the like.

At 804, the method 800 can comprise polymerizing the one or more amine monomers and the one or more electrophiles to form an ionene unit 100. The ionene unit 100 (e.g., characterized by chemical formula 700) can comprise a cation 104 distributed along a molecular backbone 102. The molecular backbone 102 can comprise one or more norspermidine structures (e.g., as illustrated in chemical formula 700). Also, the ionene unit 100 can comprise one or more functional groups 202 bonded to the molecular backbone 102 (e.g., bonded to the one or more norspermidine structures). For example, the one or more functional groups 202 can comprise carbamate functional groups, urea functional groups, and/or amide functional groups. Additionally, the ionene unit 100 can comprise a hydrophobic functional group 106 bonded to the molecular backbone 102 (e.g., via one or more cations 104). Further, the ionene unit 100 formed at 804 can have antimicrobial functionality. In one or more embodiments, the polymerizing at 804 can be performed under nitrogen gas. Additionally, the polymerizing at 804 can generate the cation through alkylation and/or quaternation with the one or more electrophiles.

During the polymerization at 804, a nitrogen atom and/or a phosphorus atom located in the one or more amine monomers (e.g., comprising an amino group of the one or more norspermidine structures) can be subject to alkylation and/or quaternization; thus, the polymerization at 804 can conduct a polymer-forming reaction (e.g., formation of the ionene unit 100) and an installation of charge (e.g., forming a cation 104, including a nitrogen cation and/or a phosphorus cation) simultaneously without a need of a catalyst. Further, one or more hydrophobic functional groups 106 can be derived from the one or more electrophiles and/or can be bonded to the one or more cations 104 as a result of the alkylation and/or quaternization process.

For example, the ionene formed at 804 can comprise one or more embodiments of the ionene unit 100 and can be characterized by one or more embodiments of chemical formula 700. For instance, the ionene unit 100 formed at 804 can comprise a molecular backbone 102 that can comprise one or more cations 104 (e.g., represented by "X" in chemical formula 700), one or more norspermidine structures (e.g., as shown in FIG. 7), one or more functional groups 202 (e.g., represented by "$R_1$" in chemical formula 700), and/or one or more hydrophobic functional groups 106 (e.g., represented by "R" in chemical formula 700). The one or more cations 104 can be nitrogen cations (e.g., protonated secondary amine cations, protonated tertiary amine cations, quaternary ammonium cations, imidazolium cations, and/or a combination thereof) and/or phosphorus cations (e.g., quaternary phosphonium cations). The cations 104 can be distributed along the molecular backbone 102 (e.g., the cations 104 can comprise one or more of the norspermidine structures). Further, one or more of the cations 104 can be bonded to one or more of the hydrophobic functional groups 106. Additionally, the ionene unit 100 formed at 804 can repeat a number of times greater than or equal to 1 and less than or equal to 1000.

Figure 9:
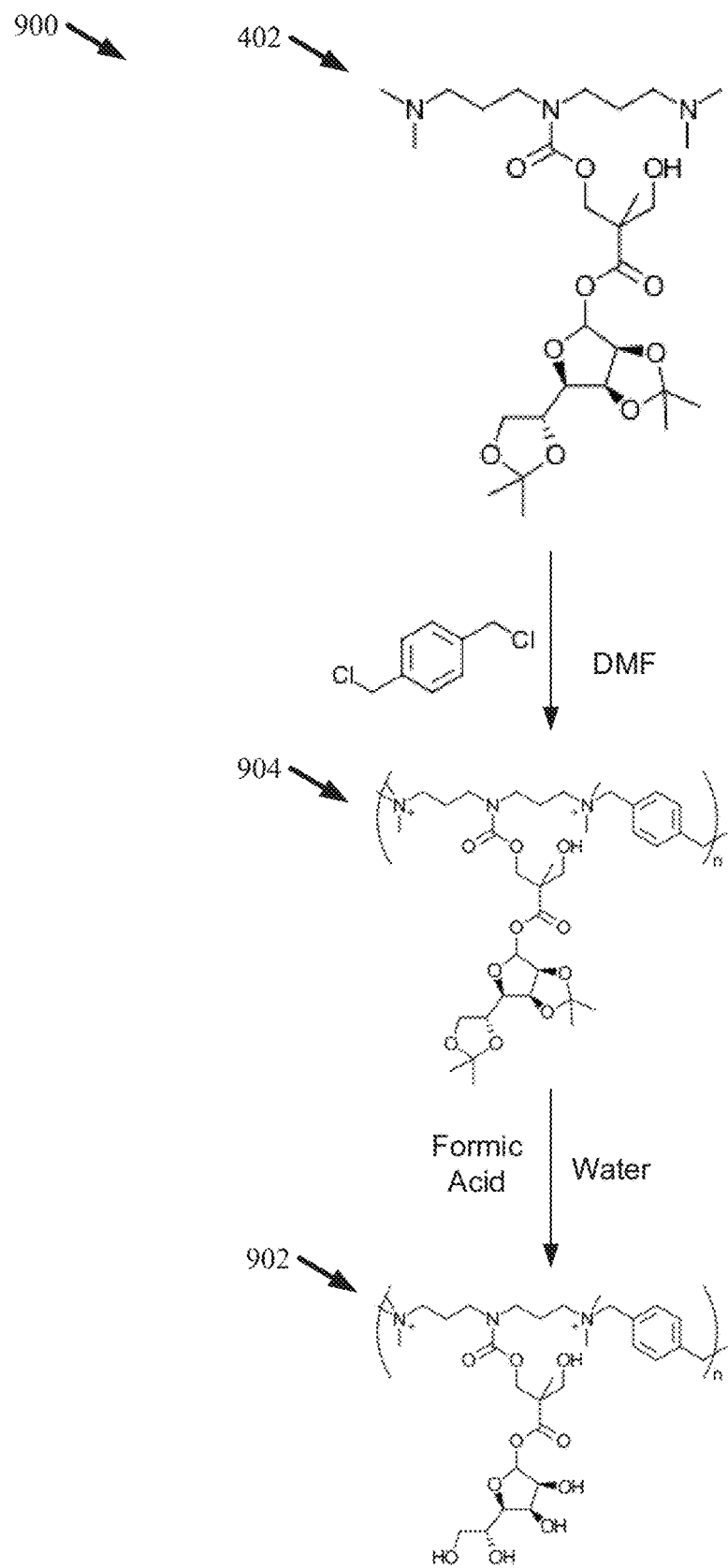
FIG. 9 illustrates a diagram of an example, non-limiting scheme that can facilitate generation of one or more ionene compositions in accordance with one or more embodiments described herein.

FIG. 9 can illustrate an example, non-limiting scheme 900 that can depict the generation of one or more ionene compositions (e.g., first ionene composition 902, which can be characterized by chemical formula 700) in accordance with one or more embodiments described herein (e.g., method 800). Repetitive description of like elements employed in other embodiments described herein is omitted for sake of brevity. Thus, scheme 900 can depict a generation of one or more ionene compositions (e.g., first ionene composition 902, which can be characterized by chemical formula 700) in accordance with the various features of method 800. While one or more particular amine monomers (e.g., first amine monomer 402), electrophiles, acids, and/or solvents are depicted; additional embodiments of scheme 900 are also envisaged. For example, the principal mechanisms of scheme 900 can be applied to any amine monomer (e.g., that can be characterized by chemical formula 200), electrophile, acid, and/or solvents in accordance with the various features described herein (e.g., with reference to chemical formula 700 and/or method 800).

As shown in FIG. 9, scheme 900 can depict a polymerization (e.g., in accordance with method 800) of one or more amine monomers (e.g., first amine monomer 402) with one or more electrophiles (e.g., p-xylylene dichloride) to generate one or more intermediate ionene compositions (e.g., intermediate ionene 904, which can be characterized by chemical formula 700). The one or more amine monomers of scheme 900 (e.g., first amine monomers 402) can comprise one or more carbamate functional groups. Additionally, the one or more carbamate functional groups can comprise structure that can include, but are not limited to: hydroxyl groups, amino groups, amide groups, ester groups, ether groups, ketone groups, carbonyl groups, alkenyl groups, carboxyl groups, mannose groups, urea groups, a combination thereof, and/or the like.

The one or more amine monomers (e.g., first amine monomer 402) can be dissolved with the one or more electrophiles (e.g., p-xylylene dichloride) in a solvent (e.g., DMF). The one or more amine monomers (e.g., first amine monomer 402), the one or more electrophiles (e.g., p-xylylene dichloride), and/or the solvent (e.g., DMF) can be stirred at a temperature greater than or equal to 15° C. and less than or equal to 150° C. for a period of time greater than or equal to 8 hours and less than or equal to 72 hours (e.g., greater than or equal to 12 hours and less than or equal to 24 hours).

Scheme 900 can further depict mixing the one or more intermediate ionene compositions (e.g., intermediate ionene 904) with an acid (e.g., formic acid) and a solvent (e.g., water) to deprotected one or more protected alcohols of the one or more intermediate ionene compositions (e.g., intermediate ionene 904) and generate one or more ionene compositions (e.g., first ionene composition 902). The deprotecting can generate one or more hydroxyl groups comprising the one or more functional groups 202 (e.g., carbamate groups) of the one or more intermediate ionene compositions (e.g., intermediate ionene 904); thereby forming one or more ionene compositions (e.g., first ionene composition 902)

The one or more ionene compositions (e.g., first ionene composition 902, which can be characterized by chemical formula 700) can comprise a molecular backbone 102 having one or more norspermidine structures bonded to a functional group 202 (e.g., a carbamate functional group). For example, the one or more ionene compositions (e.g., first ionene composition 902) can comprise one or more carbamate functional groups. Further, the one or more carbamate functional groups can comprise structures that can include, but are not limited to: hydroxyl groups, amino groups, amide groups, ester groups, ether groups, ketone groups, carbonyl groups, alkenyl groups, carboxyl groups, mannose groups, urea groups, a combination thereof, and/or the like. A polymerization (e.g., the polymerization at 804) can bond the one or more electrophiles (e.g., p-xylylene dichloride) to the one or more amine monomers (e.g., first amine monomer 402) to form the one or more ionene compositions (e.g., first ionene composition 902). For example, the polymerization (e.g., the polymerization at 804) can comprise a quaternization of one or more amino group (e.g., one or more tertiary amino groups) of the one or more norspermidine structures comprising the one or more amine monomers (e.g., first amine monomers 402). Thus, the one or more ionene compositions generated in accordance with scheme 900 (e.g., first ionene composition 902) can comprise the various features characterized by chemical formula 700 and can be generated in accordance with the various features of method 800.

Additionally, the one or more ionene compositions generated in accordance with scheme 900 (e.g., first ionene composition 902) can form monomers and or polymers (e.g., homopolymers, alternating copolymers, and/or random copolymers). For example, the "n" shown in FIG. 9 can represent an integer greater than or equal to one and less than or equal to one thousand. The one or more ionene composition generated in accordance with scheme 900 (e.g., first ionene composition 902) can have a molecular weight greater than or equal to 4,000 grams per mole (g/mol) and less than or equal to 10,000 g/mol.

Figure 10:
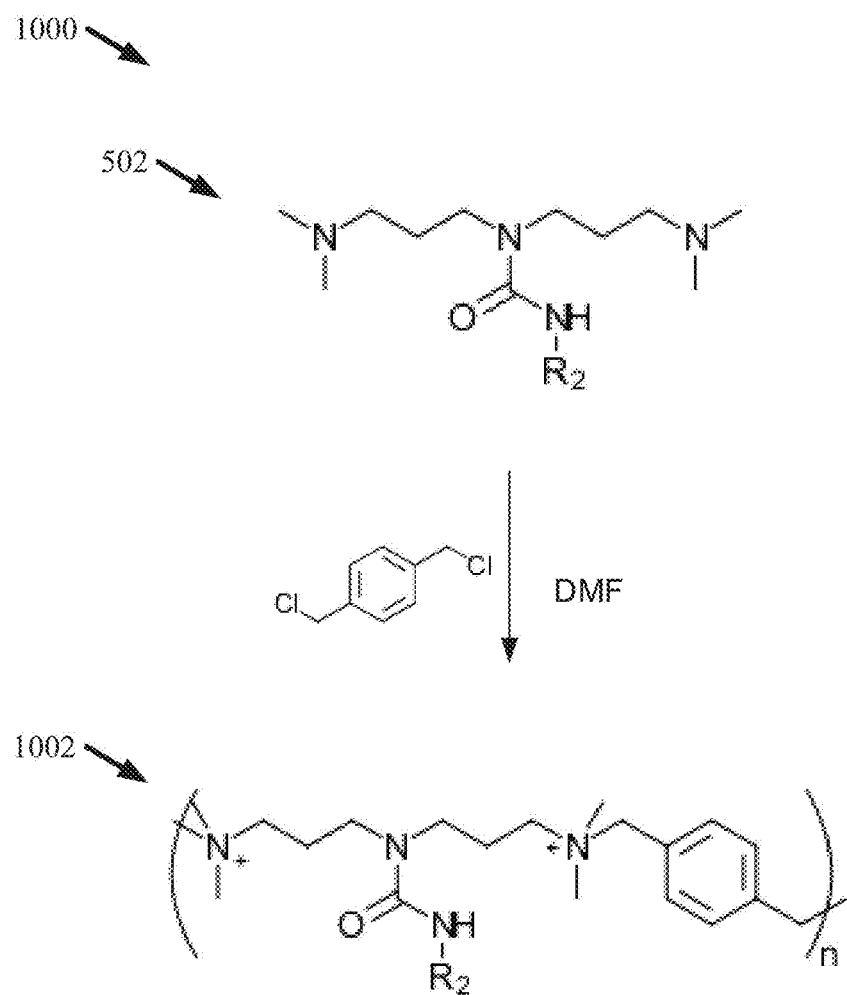
FIG. 10 illustrates a diagram of an example, non-limiting scheme that can facilitate generation of one or more ionene compositions in accordance with one or more embodiments described herein.

FIG. 10 can illustrate an example, non-limiting scheme 1000 that can depict the generation of one or more ionene compositions (e.g., second ionene composition 1002, which can be characterized by chemical formula 700) in accordance with one or more embodiments described herein (e.g., method 800). Repetitive description of like elements employed in other embodiments described herein is omitted for sake of brevity. Thus, scheme 1000 can depict a generation of one or more ionene compositions (e.g., second ionene composition 1002, which can be characterized by chemical formula 700) in accordance with the various features of method 800. While one or more particular amine monomers (e.g., second amine monomer 502), electrophiles, and/or solvents are depicted; additional embodiments of scheme 1000 are also envisaged. For example, the principal mechanisms of scheme 1000 can be applied to any amine monomer (e.g., that can be characterized by chemical formula 200), electrophile, acid, and/or solvents in accordance with the various features described herein (e.g., with reference to chemical formula 700 and/or method 800).

As shown in FIG. 10, scheme 1000 can depict a polymerization (e.g., in accordance with method 800) of one or more amine monomers (e.g., second amine monomer 502) with one or more electrophiles (e.g., p-xylylene dichloride) to generate one or more ionene compositions (e.g., second ionene composition 1002, which can be characterized by chemical formula 700). The one or more amine monomers of scheme 900 (e.g., second amine monomer 502) can comprise one or more urea functional groups. Further, the one or more urea functional groups can comprise one or more additional functional groups represented by "$R_2$" in FIG. 10. For example, the additional functional groups (e.g., represented by "$R_2$") can include, but are not limited to: phenyl groups, ethyl groups, octyl groups, propyl groups, butyl groups, a combination thereof, and/or the like.

The one or more amine monomers (e.g., second amine monomer 502) can be dissolved with the one or more electrophiles (e.g., p-xylylene dichloride) in a solvent (e.g., DMF). The one or more amine monomers (e.g., second amine monomer 502), the one or more electrophiles (e.g., p-xylylene dichloride), and/or the solvent (e.g., DMF) can be stirred at a temperature greater than or equal to 15° C. and less than or equal to 150° C. for a period of time greater than or equal to 8 hours and less than or equal to 72 hours (e.g., greater than or equal to 12 hours and less than or equal to 24 hours).

The one or more ionene compositions (e.g., second ionene composition 1002, which can be characterized by chemical formula 700) can comprise a molecular backbone 102 having one or more norspermidine structures bonded to a functional group 202 (e.g., one or more urea functional groups comprising the one or more additional functional groups "$R_2$"). For example, the one or more ionene compositions (e.g., second ionene composition 1002) can comprise one or more urea functional groups. Further, the one or more urea functional groups can comprise structures that can include, but are not limited to: phenyl groups, ethyl groups, octyl groups, propyl groups, butyl groups, a combination thereof, and/or the like. A polymerization (e.g., the polymerization at 804) can bond the one or more electrophiles (e.g., p-xylylene dichloride) to the one or more amine monomers (e.g., second amine monomer 502) to form the one or more ionene compositions (e.g., second ionene composition 1002). For example, the polymerization (e.g., the polymerization at 804) can comprise a quaternization of one or more amino groups (e.g., one or more tertiary amino groups) of the one or more norspermidine structures comprising the one or more amine monomers (e.g., second amine monomers 502). Thus, the one or more ionene compositions generated in accordance with scheme 1000 (e.g., second ionene composition 1002) can comprise the various features characterized by chemical formula 700 and can be generated in accordance with the various features of method 800.

Additionally, the one or more ionene compositions generated in accordance with scheme 900 (e.g., second ionene composition 1002) can form monomers and or polymers (e.g., homopolymers, alternating copolymers, and/or random copolymers). For example, the "n" shown in FIG. 10 can represent an integer greater than or equal to one and less than or equal to one thousand. The one or more ionene composition generated in accordance with scheme 1000 (e.g., second ionene composition 1002) can have a molecular weight greater than or equal to 1,000 g/mol and less than or equal to 8,000 g/mol.

FIG. 11 can illustrate an example, non-limiting scheme 1100 that can depict the generation of one or more ionene compositions (e.g., third ionene composition 1102, which can be characterized by chemical formula 700) in accordance with one or more embodiments described herein (e.g., method 800). Repetitive description of like elements employed in other embodiments described herein is omitted for sake of brevity. Thus, scheme 1100 can depict a generation of one or more ionene compositions (e.g., third ionene composition 1102, which can be characterized by chemical formula 700) in accordance with the various features of method 800. While one or more particular amine monomers (e.g., third amine monomer 602), electrophiles, and/or solvents are depicted; additional embodiments of scheme 1100 are also envisaged. For example, the principal mechanisms of scheme 1100 can be applied to any amine monomer (e.g., that can be characterized by chemical formula 200), electrophile, and/or solvents in accordance with the various features described herein (e.g., with reference to chemical formula 700 and/or method 800).

As shown in FIG. 11, scheme 1100 can depict a polymerization (e.g., in accordance with method 800) of one or more amine monomers (e.g., third amine monomer 602) with one or more electrophiles (e.g., p-xylylene dichloride) to generate one or more ionene compositions (e.g., third ionene composition 1102, which can be characterized by chemical formula 700). The one or more amine monomers of scheme 1100 (e.g., third amine monomers 602) can comprise one or more amide functional groups. Additionally, the one or more amide functional groups can comprise structures that can include, but are not limited to: amino groups, amide groups, ester groups, ether groups, ketone groups, carbonyl groups, alkenyl groups, carboxyl groups, urea groups, a combination thereof, and/or the like.

The one or more amine monomers (e.g., third amine monomer 602) can be dissolved with the one or more electrophiles (e.g., p-xylylene dichloride) in a solvent (e.g., DMF). The one or more amine monomers (e.g., third amine monomer 602), the one or more electrophiles (e.g., p-xylylene dichloride), and/or the solvent (e.g., DMF) can be stirred at a temperature greater than or equal to 15° C. and less than or equal to 150° C. for a period of time greater than or equal to 8 hours and less than or equal to 72 hours (e.g., greater than or equal to 12 hours and less than or equal to 24 hours).

The one or more ionene compositions (e.g., third ionene composition 1102, which can be characterized by chemical formula 700) can comprise a molecular backbone 102 having one or more norspermidine structures bonded to a functional group 202. For example, the one or more ionene compositions (e.g., third ionene composition 1102) can comprise one or more amide functional groups. Further, the one or more amide functional groups can comprise structures that can include, but are not limited to: amino groups, amide groups, ester groups, ether groups, ketone groups, carbonyl groups, alkenyl groups, carboxyl groups, urea groups, a combination thereof, and/or the like. A polymerization (e.g., the polymerization at 804) can bond the one or more electrophiles (e.g., p-xylylene dichloride) to the one or more amine monomers (e.g., third amine monomer 602) to form the one or more ionene compositions (e.g., third ionene composition 1102). For example, the polymerization (e.g., the polymerization at 804) can comprise a quaternization of one or more amino group (e.g., one or more tertiary amino groups) of the one or more norspermidine structures comprising the one or more amine monomers (e.g., third amine monomers 602). Thus, the one or more ionene compositions generated in accordance with scheme 1100 (e.g., third ionene composition 1102) can comprise the various features characterized by chemical formula 700 and can be generated in accordance with the various features of method 800.

Additionally, the one or more ionene compositions generated in accordance with scheme 1100 (e.g., third ionene composition 1102) can form monomers and or polymers (e.g., homopolymers, alternating copolymers, and/or random copolymers). For example, the "n" shown in FIG. 11 can represent an integer greater than or equal to one and less than or equal to one thousand. The one or more ionene composition generated in accordance with scheme 1100 (e.g., third ionene composition 1102) can have a molecular weight greater than or equal to 4,000 g/mol and less than or equal to 10,000 g/mol.

Figure 12:
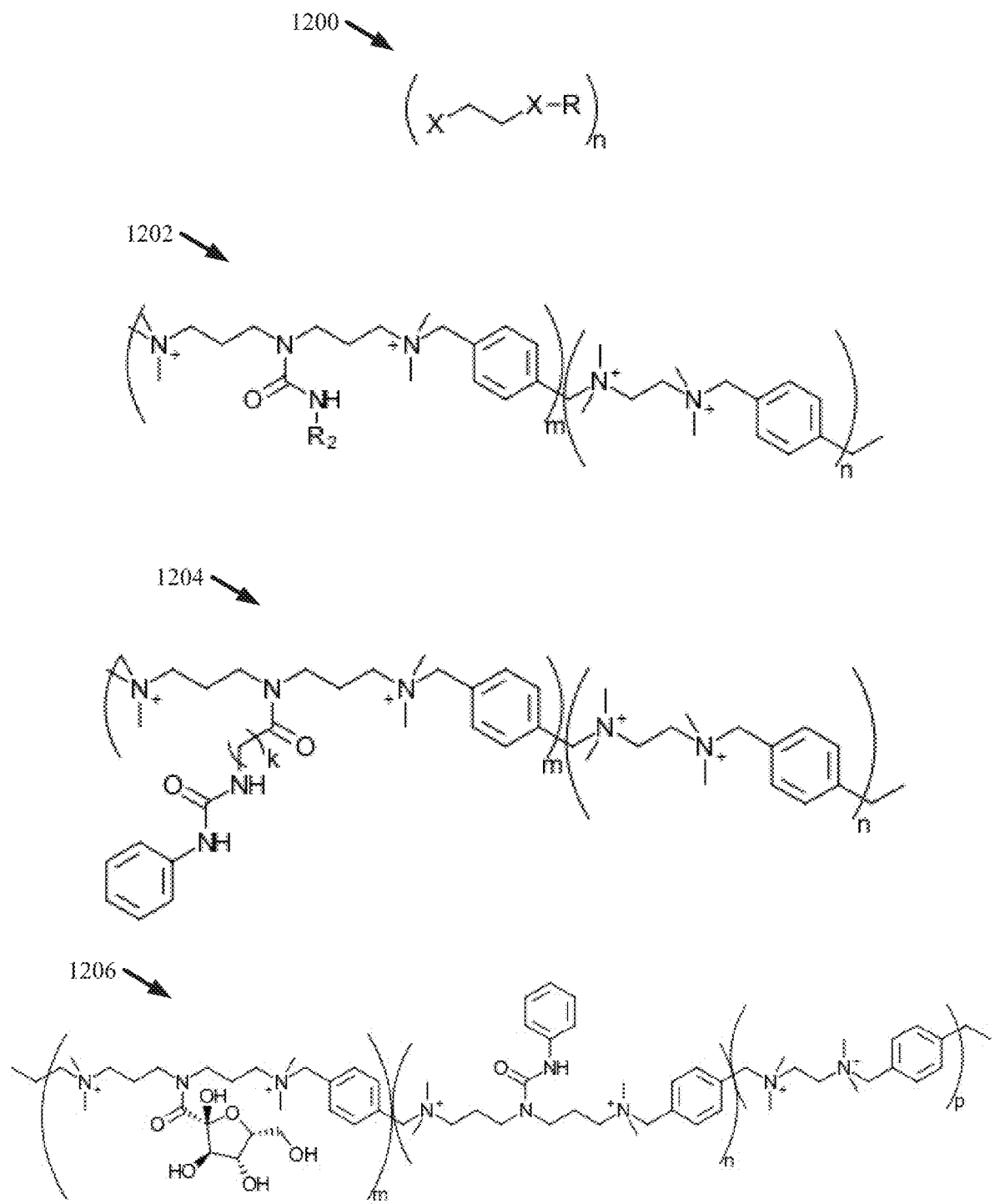
FIG. 12 illustrates a diagram of example, non-limiting ionene compositions in accordance with one or more embodiments described herein.

FIG. 12 illustrates a diagram of example, non-limiting ionene compositions in accordance with one or more embodiments described herein. Repetitive description of like elements employed in other embodiments described herein is omitted for sake of brevity. FIG. 12 shows a chemical formula 1200 that can characterize one or more ionene units 100. One or more ionene units 100 that can be characterized by chemical formula 700 can bond with one or more ionene units 100 that can be characterized by chemical formula 1200. Therefore, one or more polymers (e.g., alternating copolymer and/or random copolymers) can comprise one or more ionene units 100 that can be characterized by chemical formula 700 and/or one or more ionene units 100 that can be characterized by chemical formula 1200. The "n" shown in FIG. 12 can represent a first integer greater than or equal to zero and less than or equal to one thousand. The "m" shown in FIG. 12 can represent a second integer greater than or equal to one and less than or equal to one thousand. The "p" shown in FIG. 12 can represent a third integer greater than or equal to one and less than or equal to one thousand.

FIG. 12 shows a few example ionene compositions that can be achieved via combination of various ionene units 100 that can be characterized by chemical formula 700 and/or chemical formula 1200. However, additional ionene compositions achieved via combination of various ionene units 100 that can be characterized by chemical formula 700 and/or chemical formula 1200 are also envisaged. For example, one or more ionene compositions can comprise one or more first ionene units 100, which can be characterized by chemical formula 700 and/or comprise a first type of functional group 202 (e.g., a carbamate functional group), and one or more second ionene units 100, which can also be characterized by chemical formula 700 and/or comprise a second type of functional group 202 (e.g., a urea functional group).

One or more ionene units 100 characterized by chemical formula 1200 can comprise a molecular backbone 102. The molecular backbone 102 can comprise an alkyl structure and/or an aryl structure. For example, the molecular backbone 102 can comprise an alkyl structure having greater than or equal to two carbon atoms and less than or equal to fifteen carbon atoms.

The "X" in FIG. 12 can represent the one or more cations 104. For example, "X" can represent one or more cations 104 selected from a group that can include, but is not limited to: one or more nitrogen cations, one or more phosphorus cations, and/or a combination thereof. For instance, "X" can represent one or more nitrogen cations selected from a group that can include, but is not limited to: one or more protonated secondary amine cations, one or more protonated tertiary amine cations, one or more quaternary ammonium cations, one or more imidazolium cations, and/or a combination thereof. In another instance, "X" can represent one or more phosphorus cations selected from a group that can include, but is not limited to: one or more protonated secondary phosphine cations, one or more protonated tertiary phosphine cations, one or more quaternary phosphonium cations, and/or a combination thereof.

The one or more cations 104 (e.g., represented by "X" in chemical formula 1200) can be comprise the molecular backbone 102. As shown in FIG. 12, in various embodiments, an ionene unit 100 characterized by chemical formula 1200 can comprise cations 104 (e.g., represented by "X") at a plurality of locations along the molecular backbone 102. For example, cations 104 can be located at either end of the molecular backbone 102 (e.g., as illustrated in FIG. 12). However, in one or more embodiments of chemical formula 1200, the molecular backbone 102 can comprise less or more cations 104 than the two illustrated in FIG. 12.

Further, the "R" shown in FIG. 12 can represent the one or more hydrophobic functional groups 106 in accordance with the various embodiments described herein. For example, the one or more hydrophobic functional groups 106 can comprise one or more alkyl groups and/or one or more aryl groups. For instance, the hydrophobic functional group 106 can be derived from one or more dialkyl halides. The one or more hydrophobic functional groups 106 (e.g., represented by "R" in FIG. 12) can be covalently bonded to one or more of the cations 104 (e.g., represented by "X" in FIG. 12) and/or the molecular backbone 102, which can comprise the one or more cations 104 (e.g., represented by "X" in FIG. 12).

The fourth ionene composition 1202 shown in FIG. 12 can comprise one or more first ionene units 100, which can be characterized by chemical formula 700, covalently bonded to one or more second ionene units 100, which can be characterized by chemical formula 1200. The fourth ionene composition 1202 can be an alternating copolymer and/or a random copolymer.

The one or more first ionene units 100 of the fourth ionene composition 1202, which can be characterized by chemical formula 700, can comprise a urea functional group as the functional group 202. Further, the urea functional group can comprise one or more additional functional groups represented by "$R_2$" in FIG. 12. Example additional functional groups (e.g., represented by "$R_2$") can include, but are not limited to: phenyl groups, ethyl groups, octyl groups, propyl groups, butyl groups, a combination thereof, and/or the like. Additionally, the one or more first ionene units 100 can comprise one or more quaternary ammonium cations, and/or one or more hydrophobic functional group 106 comprising a benzene ring.

The one or more second ionene units 100 of the fourth ionene composition 1202, which can be characterized by chemical formula 1200, can also comprise one or more quaternary ammonium cations, and/or one or more hydrophobic functional group 106 comprising a benzene ring. Additionally, one or more second ionene units 100 can be bonded to the one or more first ionene units 100 via one or more hydrophobic functional groups 106.

The fifth ionene composition 1204 shown in FIG. 12 can comprise one or more first ionene units 100, which can be characterized by chemical formula 700, covalently bonded to one or more second ionene units 100, which can be characterized by chemical formula 1200. The fifth ionene composition 1204 can be an alternating copolymer and/or a random copolymer.

The one or more first ionene units 100 of the fifth ionene composition 1204, which can be characterized by chemical formula 700, can comprise an amide functional group as the functional group 202. Additionally, the one or more amide functional groups can comprise one or more structures that can include alky structures, urea structures, and/or aryl structures. Also, "k" shown in FIG. 12 can represent a fourth integer greater than or equal to 1 and less than or equal to 10. Further, the one or more first ionene units 100 can comprise one or more quaternary ammonium cations, and/or one or more hydrophobic functional group 106 comprising a benzene ring.

The one or more second ionene units 100 of the fifth ionene composition 1204, which can be characterized by chemical formula 1200, can also comprise one or more quaternary ammonium cations, and/or one or more hydrophobic functional group 106 comprising a benzene ring. Additionally, one or more second ionene units 100 can be bonded to the one or more first ionene units 100 via one or more hydrophobic functional groups 106.

The sixth ionene composition 1206 shown in FIG. 12 can comprise one or more first ionene units 100, which can be characterized by chemical formula 700, one or more second ionene units 100, which can be characterized by chemical formula 700, and/or one or more third ionene units 100, which can be characterized by chemical formula 1200, bonded together. The sixth ionene composition 1206 can be an alternating copolymer and/or a random copolymer.

The one or more first ionene units 100 of the sixth ionene composition 1206, which can be characterized by chemical formula 700, can comprise a carbamate functional group as the functional group 202. Additionally, the carbamate functional group can comprise a deprotected mannose structure. Further, the one or more first ionene units 100 can comprise one or more quaternary ammonium cations, and/or one or more hydrophobic functional groups 106 comprising a benzene ring.

In one or more embodiments, the first ionene units 100 of the sixth ionene composition 1206 can comprise an independent chemical composition, absent the second ionene units 100 and/or the third ionene units 100. However, chemical compounds (e.g., ionenes and/or polyionenes) comprising ionene units containing mannose groups without other functionalities can have relatively low antimicrobial activity as the presence of the mannose groups can shield cationic charges and reduce overall hydrophobicity of the chemical compound. Copolymerization with ionene units 100 containing other functional groups can offer intracellular targeting ability without compromising antimicrobial potency. Table 1, presented below, can depict the antimicrobial activity of the first ionene units 100 regarding minimum inhibitory concentrations (MIC) in micrograms per milliliter (µg/mL) of ionene compositions of only the first ionene units 100 regarding *Staphylococcus aureus* ("SA"), *Escherichia coli* ("EC"), *Pseudomonas aeruginosa* ("PA"), and/or *Candida albicans* ("CA"). Table 1 also depicts the MIC in µg/mL of the subject ionene composition that leads to lysis of 50% of subject rat red blood cells ("HC$_{50}$).

TABLE 1

| SA | EC | PA | CA | HC$_{50}$ |
|---|---|---|---|---|
| 63 | >1000 | 500 | 250 | >2000 |

The one or more second ionene units 100 of the sixth ionene composition 1206, which can be characterized by chemical formula 700, can comprise a urea functional group as the functional group 202. Further, the urea functional group can comprise a phenyl group. Additionally, the one or more first ionene units 100 can comprise one or more quaternary ammonium cations, and/or one or more hydrophobic functional groups 106 comprising a benzene ring.

The one or more third ionene units 100 of the sixth ionene composition 1206, which can be characterized by chemical formula 1200, can also comprise one or more quaternary ammonium cations, and/or one or more hydrophobic functional groups 106 comprising a benzene ring. Additionally, one or more third ionene units 100 can be bonded to the one or more first ionene units 100 and/or one or more of the second ionene units 100 via one or more hydrophobic functional groups 106.

FIG. 13 can illustrate a diagram of an example, non-limiting chart 1300 that can depict one or more structural characteristics and/or one or more antimicrobial functionality of the fourth ionene composition 1202. Repetitive description of like elements employed in other embodiments described herein is omitted for sake of brevity.

The first column 1302 of chart 1300 can depict the second functional group (e.g., represented by "R$_2$" in FIG. 12) comprising the fourth ionene composition 1202 for the subject evaluation. The second column 1304 of chart 1300 can depict a ratio of the first ionene unit 100 to the second ionene unit 100 comprising the fourth ionene composition 1202 for the subject evaluation. The third column 1306 of the chart 1300 can depict the number average molecular weight ($M_n$) as determined by size exclusion chromatography (SEC) regarding the subject ionene composition. The fourth column 1308 of the chart 1300 can depict polydispersity regarding the subject ionene composition.

The fifth column 1310 of chart 1300 can depict the minimum inhibitory concentration (MIC) in micrograms per milliliter (µg/mL) of the subject ionene composition regarding *Staphylococcus aureus* ("SA"). The sixth column 1312 of chart 1300 can depict the MIC in µg/mL of the subject ionene composition regarding *Escherichia coli* ("EC"). The seventh column 1314 of chart 1300 can depict the MIC in µg/mL of the subject ionene composition regarding *Pseudomonas aeruginosa* ("PA"). The eighth column 1316 of chart 1300 can depict the MIC in µg/mL of the subject ionene composition regarding *Candida albicans* ("CA"). The ninth column 1318 of chart 1300 can depict the concentration of the subject ionene composition that leads to lysis of 50% of the subject red blood cells ("HC$_{50}$") in µg/mL of the subject polyionene composition regarding rat red blood cells. FIG. 13 can illustrate that copolymerization of one or more ionene units 100 that can be characterized by chemical formula 700 with one or more ionene units 100 that can be characterized by chemical formula 1200 can form ionene compositions with high antimicrobial activity and low toxicity towards mammalian cells. For example, the ionene of more ionene units 100 that can be characterized by chemical formula 1200 can hinder formation of intramolecular hydrogen-bonding interactions.

FIG. 14 can illustrate a diagram of an example, non-limiting chart 1400 that can depict one or more structural characteristics and/or one or more antimicrobial functionality of the fifth ionene composition 1204. Repetitive description of like elements employed in other embodiments described herein is omitted for sake of brevity.

The first column 1402 of chart 1400 can depict the "k" value (e.g., represented in FIG. 12) comprising the fifth ionene composition 1204 for the subject evaluation. The second column 1404 of chart 1400 can depict a ratio of the first ionene unit 100 to the second ionene unit 100 comprising the fifth ionene composition 1204 for the subject evaluation. The third column 1406 of the chart 1400 can depict the number average molecular weight ($M_e$) as determined by size exclusion chromatography (SEC) regarding the subject ionene composition. The fourth column 1408 of the chart 1400 can depict polydispersity regarding the subject ionene composition.

The fifth column 1410 of chart 1400 can depict the minimum inhibitory concentration (MIC) in micrograms per milliliter (μg/mL) of the subject ionene composition regarding *Staphylococcus aureus* ("SA"). The sixth column 1412 of chart 1400 can depict the MIC in μg/mL of the subject ionene composition regarding *Escherichia coli* ("EC"). The seventh column 1414 of chart 1400 can depict the MIC in μg/mL of the subject ionene composition regarding *Pseudomonas aeruginosa* ("PA"). The eighth column 1416 of chart 1400 can depict the MIC in μg/mL of the subject ionene composition regarding *Candida albicans* ("CA"). The ninth column 1418 of chart 1400 can depict the $HC_{50}$ in μg/mL of the subject ionene composition regarding rat red blood cells.

Figure 15:
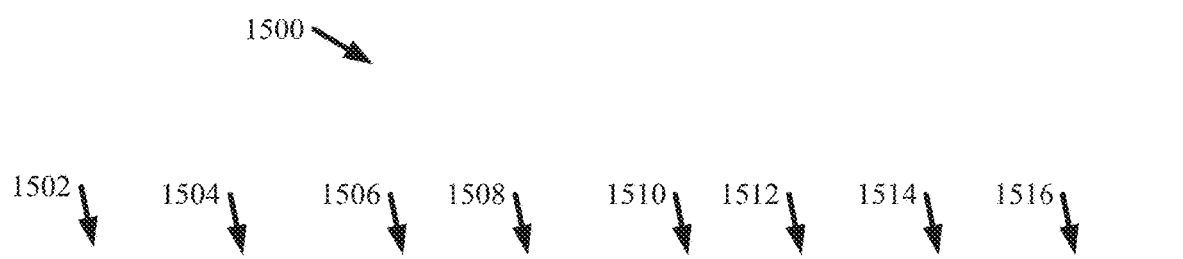
FIG. 15 illustrates a diagram of an example, non-limiting chart that can depict structural characteristics and/or antimicrobial functionality of one or more ionene compositions in accordance with one or more embodiments described herein.

FIG. 15 can illustrate a diagram of an example, non-limiting chart 1500 that can depict one or more structural characteristics and/or one or more antimicrobial functionality of the sixth ionene composition 1206. Repetitive description of like elements employed in other embodiments described herein is omitted for sake of brevity.

The first column 1502 of chart 1500 can depict a first ratio of the first ionene unit 100, the second ionene unit 100, and/or the third ionene unit 100 comprising the sixth ionene composition 1206 for a subject evaluation. The second column 1504 of chart 1500 can depict a second ratio of the first ionene unit 100, the second ionene unit 100, and/or the third ionene unit 100 comprising the sixth ionene composition 1206 for a subject evaluation. The third column 1502 of chart 1500 can depict a third ratio of the first ionene unit 100, the second ionene unit 100, and/or the third ionene unit 100 comprising the sixth ionene composition 1206 for a subject evaluation.

The fourth column 1508 of chart 1500 can depict the minimum inhibitory concentration (MIC) in micrograms per milliliter (μg/mL) of the subject ionene composition regarding *Staphylococcus aureus* ("SA"). The fifth column 1510 of chart 1500 can depict the MIC in μg/mL of the subject ionene composition regarding *Escherichia coli* ("EC"). The sixth column 1512 of chart 1500 can depict the MIC in μg/mL of the subject ionene composition regarding *Pseudomonas aeruginosa* ("PA"). The seventh column 1514 of chart 1500 can depict the MIC in μg/mL of the subject ionene composition regarding *Candida albicans* ("CA"). The eighth column 1516 of chart 1500 can depict the $HC_{50}$ in μg/mL of the subject ionene composition regarding rat red blood cells.

Figure 16A:
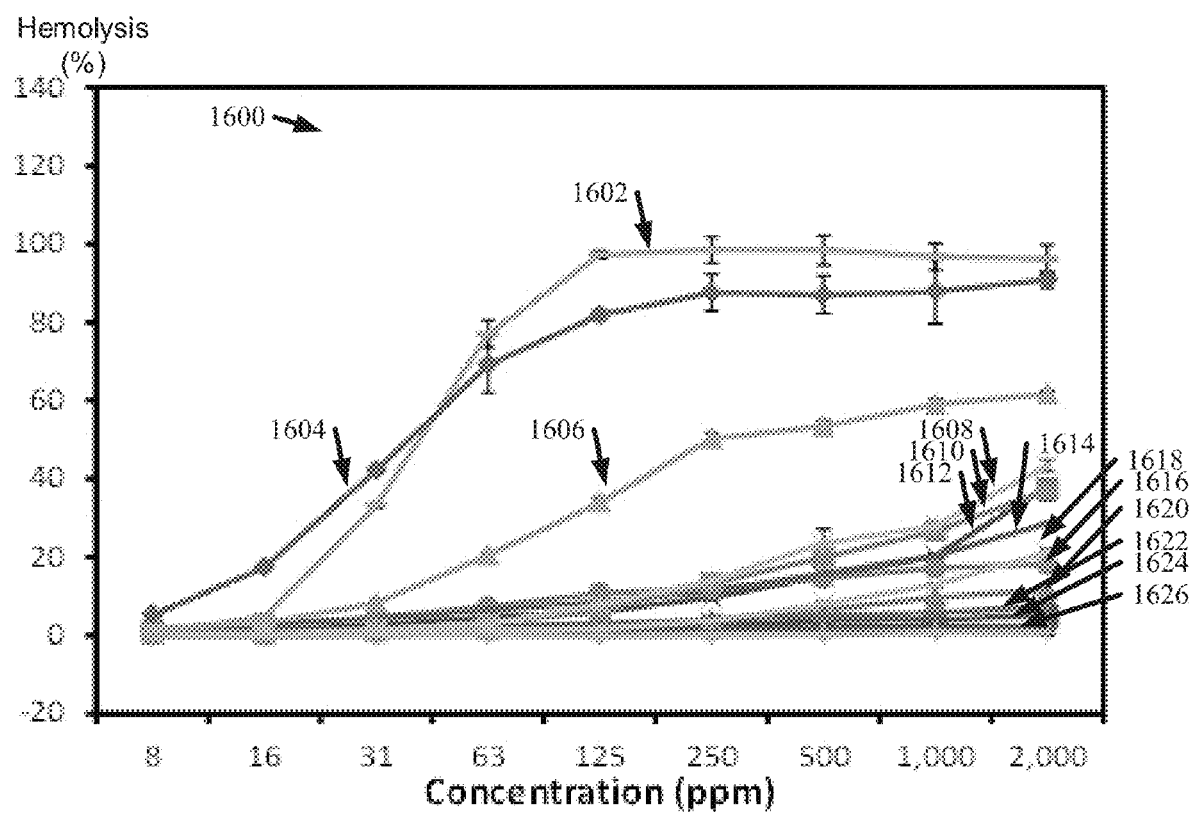
FIG. 16A illustrates a diagram of an example, non-limiting graph that can depict hemolysis activity of one or more ionene composition in accordance with one or more embodiments described herein.

FIG. 16A illustrates a diagram of an example, non-limiting first graph 1600 that can depict the hemolytic activity of various ionene compositions at various concentrations in accordance with the one or more embodiments described herein. Repetitive description of like elements employed in other embodiments described herein is omitted for sake of brevity. For example, FIG. 16A can show hemolytic activity of one or more ionene compositions at concentrations ranging from 8 parts per million (ppm) to 2000 ppm. The hemolytic activity depicted in the first graph 1600 can regard rat red blood cells.

The first line 1602 of the first graph 1600 can regard the fourth ionene composition 1202 comprising an octyl group and/or a m/n ratio of 100/0. The second line 1604 of the first graph 1600 can regard the fourth ionene composition 1202 comprising an octyl group and/or a m/n ratio of 50/50. The third line 1606 of the first graph 1600 can regard the fifth ionene composition 1204 comprising a "k" value of 3 and/or a m/n ratio of 50/50. The fourth line 1608 of the first graph 1600 can regard the fifth ionene composition 1204 comprising a "k" value of 5 and/or a m/n ratio of 50/50. The fifth line 1610 of the first graph 1600 can regard the fifth ionene composition 1204 comprising a "k" value of 3 and/or a m/n ratio of 100/0. The sixth line 1612 of the first graph 1600 can regard the fourth ionene composition 1202 comprising a phenyl group and/or a m/n ratio of 100/0. The seventh line 1614 of the first graph 1600 can regard the fourth ionene composition 1202 comprising an i-propyl group and/or a m/n ratio of 50/50. The eighth line 1616 of the first graph 1600 can regard the fourth ionene composition 1202 comprising an ethyl group and/or a m/n ratio of 50/50. The ninth line 1618 of the first graph 1600 can regard the fifth ionene composition 1204 comprising a "k" value of 5 and/or a m/n ratio of 100/0. The tenth line 1620 of the first graph 1600 can regard the fourth ionene composition 1202 comprising a s-butyl group and/or a m/n ratio of 100/0. The eleventh line 1622 of the first graph 1600 can regard the fourth ionene composition 1202 comprising a s-butyl group and/or a m/n ratio of 50/50. The twelfth line 1624 of the first graph 1600 can regard the fourth ionene composition 1202 comprising a phenyl group and/or a m/n ratio of 50/50. The thirteenth line 1626 of the first graph 1600 can regard the fourth ionene composition 1202 comprising an ethyl group and/or a m/n ratio of 100/0.

Figure 16B:
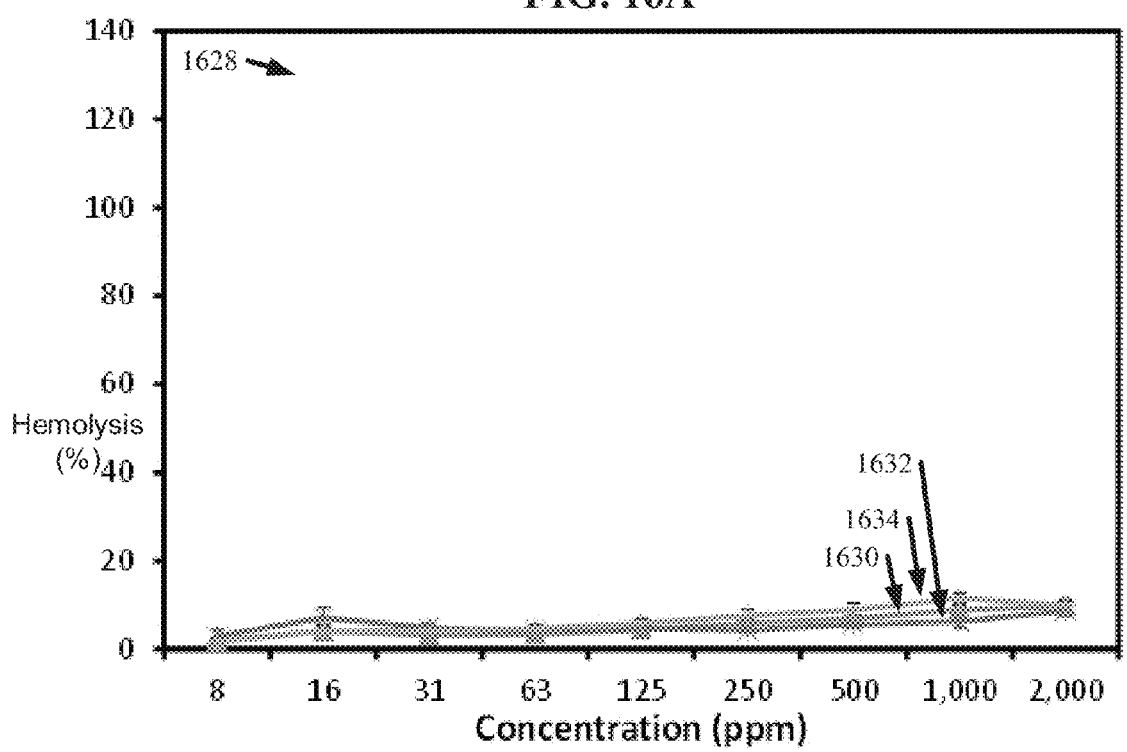
FIG. 16B illustrates another diagram of an example, non-limiting graph that can depict hemolysis activity of one or more ionene composition in accordance with one or more embodiments described herein.

FIG. 16B illustrates a diagram of an example, non-limiting second graph 1628 that can depict the hemolytic activity of various ionene compositions at various concentrations in accordance with the one or more embodiments described herein. Repetitive description of like elements employed in other embodiments described herein is omitted for sake of brevity. For example, FIG. 16B can show hemolytic activity of one or more ionene compositions at concentrations ranging from 8 parts per million (ppm) to 2000 ppm. The hemolytic activity depicted in the second graph 1628 can regard rat red blood cells.

The first line 1630 of the second graph 1628 can regard the sixth ionene composition 1206 with an n/(m+n+p) ratio of 0. The second line 1632 of the second graph 1628 can regard the sixth ionene composition 1206 with an n/(m+n+p) ratio of 0.05. The third line 1634 of the second graph 1628 can regard the sixth ionene composition 1206 with an n/(m+n+p) ratio of 0.15.

FIG. 17 illustrates another flow diagram of an example, non-limiting method 1700 of killing a pathogen, preventing the growth of a pathogen, and/or preventing contamination by a pathogen. Repetitive description of like elements employed in other embodiments described herein is omitted for sake of brevity. Example pathogens include, but are not limited to: Gram-negative bacteria, Gram-positive bacteria, fungi, yeast, a combination thereof, and/or the like.

At 1702, the method 1700 can comprise contacting the pathogen with a chemical compound (e.g., an ionene, a polyionene, a monomer, and/or a polymer). The chemical compound can comprise an ionene unit 100 (e.g., characterized by chemical formula 700 and/or 1200). The ionene unit 100 can comprise a cation 104 (e.g., a nitrogen cation cation) distributed along a molecular backbone 102 that can comprise one or more norspermidine structures (e.g., derived from 3,3'-iminobis(N, N-dimethyl propylamine). Further, the ionene unit can comprise one or more functional groups 202 bonded to the one or more norspermidine structures. For example, the one or more functional groups 202 can comprise carbamate functional groups, urea functional groups, and/or amide functional groups. The ionene unit 100 can have antimicrobial functionality.

At 1704, the method 1700 can comprise electrostatically disrupting a membrane of the pathogen (e.g., via lysis process 108) upon contacting the pathogen with the chemical compound (e.g., an ionene unit 100 characterized by chemical formula 700 and/or 1200). Additionally, contacting the pathogen with the chemical compound (e.g., ionene unit 100 characterized by chemical formula 700 and/or 1200) can disrupt the membrane through hydrophobic membrane integration (e.g., via lysis process 108).

The ionene unit 100 that can comprise the chemical compound contacting the pathogen at 1702 can comprise one or more embodiments of the ionene unit 100 and can be characterized by one or more embodiments of chemical formula 700 and/or 1200. For instance, the ionene unit 100 can comprise a molecular backbone 102 that can comprise one or more cations 104 (e.g., represented by "X" in chemical formula 700 and/or 1200), one or more norspermidine structures (e.g., as shown in FIGS. 7-12), one or more hydrophobic functional groups 106 (e.g., represented by "R" in chemical formula 700 and/or 1200), and/or one or more functional groups 202. The one or more cations 104 can be nitrogen cations (e.g., quaternary ammonium cations, imidazolium cations, and/or a combination thereof) and/or phosphorus cations (e.g., quaternary phosphonium cations). Further, one or more of the cations 104 can be bonded to one or more of the hydrophobic functional groups 106. Additionally, the ionene unit 100 can repeat a number of times greater than or equal to 1 and less than or equal to 1000. Therefore, the ionene unit 100 contacting the pathogen at 1702 can comprise any and all the features of various embodiments described herein.

The various structures (e.g., described regarding FIGS. 1-2, 7, and/or 12), compositions (e.g., described regarding FIGS. 4-6 and/or 9-16), and/or methods (e.g., described regarding FIGS. 3, 8, and/or 17) described herein can regard chemical compounds that can be incorporated into a variety of applications. For example, said applications can include cleaning, sanitizing, disinfecting, and/or otherwise treating various articles such as, but not limited to: food packaging, medical devices, floor surfaces, furniture surfaces, wound care instruments (e.g., bandages and/or gauss), building surfaces, plants (e.g., agricultural crops), ground surfaces, farming equipment, beds, sheets, clothes, blankets, shoes, doors, door frames, walls, ceilings, mattresses, light fixtures, facets, switches, sinks, grab rails, remote controls, vanities, computer equipment, carts, trolleys, hampers, bins, a combination thereof, and/or the like. In another example, said applications can include pharmaceuticals, pharmaceutical salts, hygiene products (e.g., soaps and/or shampoos), and/or the like. In a further example, said applications can include agricultural sprays and/or aqueous solutions that can facilitate processing crops for consumption.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

What has been described above include mere examples of systems, compositions, and methods. It is, of course, not possible to describe every conceivable combination of reagents, products, solvents, and/or articles for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim. The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:
1. A monomer comprising:
a structure characterized by a formula selected from the group consisting of

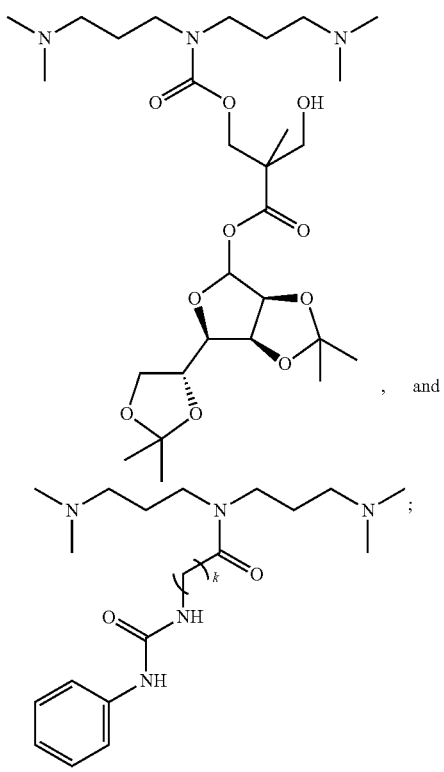

wherein "k" corresponds to an integer greater than or equal to 1 and less than or equal to 10.
2. The monomer of claim 1, wherein the structure is characterized by the formula:
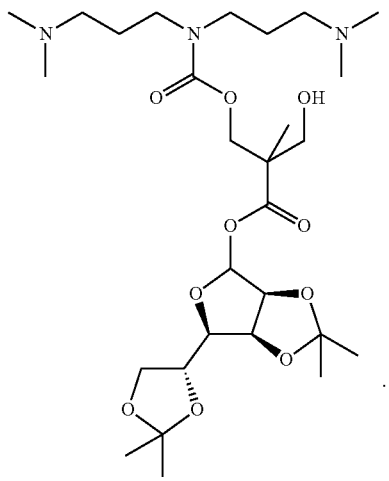
3. The monomer of claim 1, wherein the structure is characterized by the formula:
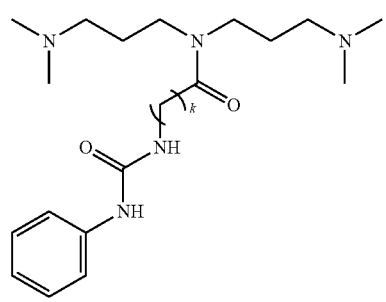
* * * * *